(12) United States Patent
Nightingale et al.

(10) Patent No.: US 7,998,181 B2
(45) Date of Patent: *Aug. 16, 2011

(54) SYSTEM AND METHOD UTILIZING GUIDED FLUORESCENCE FOR HIGH INTENSITY APPLICATIONS

(75) Inventors: John L. Nightingale, Portola Valley, CA (US); Gregory J. Spooner, Kensington, CA (US); David A. Gollnick, San Francisco, CA (US); Dean A. MacFarland, Magnolia, MA (US)

(73) Assignee: Cutera, Inc., Brisbane, CA (US)

( * ) Notice: Subject to any disclaimer, the term of this patent is extended or adjusted under 35 U.S.C. 154(b) by 1401 days.

This patent is subject to a terminal disclaimer.

(21) Appl. No.: 11/504,399

(22) Filed: Aug. 15, 2006

(65) Prior Publication Data
US 2006/0282137 A1    Dec. 14, 2006

Related U.S. Application Data

(63) Continuation of application No. 10/897,352, filed on Jul. 22, 2004, now Pat. No. 7,208,007.

(60) Provisional application No. 60/493,171, filed on Aug. 7, 2003, provisional application No. 60/582,489, filed on Jun. 24, 2004.

(51) Int. Cl.
*A61B 18/18* (2006.01)
(52) U.S. Cl. .......... 607/90; 128/898; 362/551; 362/555; 606/9; 607/88; 607/94
(58) Field of Classification Search ................. 128/898; 362/551–555; 606/9; 607/88–94
See application file for complete search history.

(56) References Cited

U.S. PATENT DOCUMENTS

| | | | |
|---|---|---|---|
| 4,262,206 A | 4/1981 | Viehmann | 250/483.1 |
| 4,371,897 A | 2/1983 | Kramer | 358/474 |
| 5,128,846 A * | 7/1992 | Mills et al. | 362/224 |
| 5,409,483 A | 4/1995 | Campbell et al. | 606/15 |
| 5,579,429 A | 11/1996 | Naum | 385/143 |
| 5,721,795 A | 2/1998 | Pelka | 385/37 |
| 5,805,623 A | 9/1998 | Utano et al. | 372/23 |
| 5,806,955 A | 9/1998 | Parkyn et al. | |
| 6,272,269 B1 | 8/2001 | Naum | 385/43 |
| 6,383,176 B1 | 5/2002 | Connors et al. | 606/9 |
| 6,485,484 B1 | 11/2002 | Connors et al. | 606/9 |
| 6,744,960 B2 | 6/2004 | Pelka | 385/130 |
| 6,784,603 B2 | 8/2004 | Pelka et al. | 313/113 |

(Continued)

OTHER PUBLICATIONS

Daniel A. Steigerwald et al., "Illumination With Solid State Lighting Technology," *IEEE Journal on Selected Topics in Quantum Electronics*, vol. 8, No. 2, Mar./Apr. 2002, pp. 310-319.

(Continued)

*Primary Examiner* — Ahmed Farah
*Assistant Examiner* — Aaron Roane
(74) *Attorney, Agent, or Firm* — Morrison & Foerster LLP

(57) ABSTRACT

A fluorescence concentrator system that provides for high brightness light source. The system can include a host doped with fluorescent material, which is optically pumped by an adjacent illumination source. The fluorescence concentrator captures a portion of the isotropically emitted fluorescent light and guides it to an output surface. The fluorescent energy emerging the output surface provides a high brightness light source suitable for a number of applications. For example, the fluorescence concentrator system can be used as the light source in a medical apparatus suitable for various aesthetic procedures. Further aspects of the fluorescent concentrator system can include providing for controlling the illumination source to output pumping energy suitable for high energy applications.

15 Claims, 10 Drawing Sheets

U.S. PATENT DOCUMENTS

| | | | | |
|---|---|---|---|---|
| 6,981,970 | B2 | 1/2006 | Karni | 606/9 |
| 7,083,610 | B1 | 8/2006 | Murray et al. | 606/9 |
| 2002/0127224 | A1* | 9/2002 | Chen | 424/130.1 |
| 2003/0044114 | A1 | 3/2003 | Pelka | 385/31 |
| 2003/0053776 | A1 | 3/2003 | Dejneka et al. | 385/123 |
| 2003/0233138 | A1 | 12/2003 | Spooner | 607/93 |
| 2005/0063197 | A1 | 3/2005 | Nightingale et al. | 362/551 |
| 2005/0107852 | A1 | 5/2005 | Levernier et al. | 607/89 |
| 2005/0137655 | A1 | 6/2005 | MacFarland et al. | 607/88 |

OTHER PUBLICATIONS

W. A. Shurcliff et al., "The Trapping of Fluorescent Light Produced within Objects of High Geometrical Symmetry," *Journal of the Optical Society of America*, vol. 39, No. 11, Nov. 1949, pp. 912-916.

W. A. Shurcliff, "Radiance Amplification by Multi-Stage Fluorescence System," *Journal of the Optical Society of America*, vol. 41, No. 3, Mar. 1951, p. 209.

L. Reiffel et al., "Some Considerations on Luminescent Fiber Chambers and Intensifier Screens," *The Review of Scientific Instruments*, vol. 31, No. 10, Oct. 1960, pp. 1136-1142.

Gunter Keil, "Radiance Amplification by a Fluorescence Radiation Converter" *Journal of Applied Physics*, vol. 40, No. 9, Aug. 1969, pp. 3544-3547.

W. H. Weber et al., "Luminescent greenhouse collector for solar radiation," *Applied Optics*, vol. 15, No. 10, Oct. 1976, pp. 2299-2300.

S. A. Evenson et al., "Thin-film luminescent concentrators for integrated devices," *Applied Optics*, vol. 34, No. 31, Nov. 1, 1995, pp. 7231-7238.

Paul D. Swift et al., "Light to light efficiencies in Luminescent Solar Concentrators," *Proceeding of the SPIE*, vol. 3789, Jul. 1999, pp. 21-28.

Keith Barnham et al. "Quantum-dot concentrator and thermodynamic model for the global redshift," *Applied Physics Letters*, vol. 76, No. 9, Feb. 28, 2000, pp. 1197-1199.

Mitsunori Saito et al., "Bright afterglow illuminator made of phosphorescent material and fluorescent fibers," *Applied Optics*, vol. 39, No. 24, Aug. 20, 2000, pp. 4366-4371.

Mitsunori Saito et al., "Axial and Radial Fluorescent of Dye-Doped Polymer Fiber," *Journal of Lightwave Technology*, vol. 19, No. 7, Jul. 2001, pp. 982-987.

A. J. Chatten et al., "A new approach to modeling quantum dot concentrators" *Solar Energy Materials & Solar Cells*, vol. 75, (2003), pp. 363-371.

Paul D. Swift et al., "Color considerations in fluorescent solar concentrator stacks" *Applied Optics*, vol. 42, No. 25, Sep. 1, 2003, pp. 5112-5117.

"Scintillating Optical Fibers", Bicron/Saint Gobain, Newbury, Ohio, 2002, 8 pages in length.

Andrews et al., "Luminescent Solar Collectors Based on Fluorescent Glasses", Journal of Luminescence, vol. 24/25, 1981, pp. 877-880.

Binns et al., "Scintillator-Fiber Charged-Particle Track-Imaging Detector", Nuclear Instruments and Methods, vol. 216, 1983, pp. 475-480.

Chiron, Bernard, "Highly efficient plastic optical fluorescent fibers and sensors", Proceedings of the SPIE, vol. 1592, 1991, pp. 86-95.

Chung et al., "Effects of light on scintillating fibers", Proceedings of the SPIE, vol. 2007, 1993, pp. 41-48.

Fiiloux et al., "Fluorescent solar concentrators using liquid solutions", Revue de Physique Appliquee, vol. 18, 1983, pp. 273-279.

Garwin, Richard L. "The Collection of Light from Scintillation Counters", The Review of Scientific Instruments, vol. 31, 1960, pp. 1010-1011.

Neuroth et al., "Glasses for Luminescent Solar Concentrators", Solar Energy Materials, vol. 16, 1987, pp. 235-242.

Pandey et al., "Solar energy concentrator based on uranyl-doped PMMA", Solar Energy Materials, vol. 21, 1991, pp. 327-334.

Plastifo, "Fluorescent Plastic Optical Fibers", Optectron Industries, Les Ulis Cedex, France, May 2003, 11 pages in length.

Reisfeld et al., "Photostable solar concentrators based on fluorescent glass films", Solar Energy Materials and Solar Cells, vol. 33, 1994, pp. 417-427.

Ruchti, R., "Performance of multiclad scintillating and waveguide optical fibers read out with visible light photon counters", Proceedings of the SPIE, vol. 2007, Feb. 1993, pp. 78-94.

Sims, Paul E., "Solar Battery Recharge Options for Unattended Ground Sensors", Proceedings of the SPIE, vol. 4393, 2001, pp. 230-240.

Sulima et al., "High-performance monolithic AlGaAs/GaAs photovoltaic arrays coupled to scintillating fibers for UGS application", Proceedings of the SPIE, vol. 4743, 2002, pp. 120-128.

White, T. O., "Scintillating Fibres", Nuclear Instruments and Methods in Physics Research, vol. A273, 1988, pp. 820-825.

* cited by examiner

SYSTEM AND METHOD UTILIZING GUIDED FLUORESCENCE FOR HIGH INTENSITY APPLICATIONS

RELATED APPLICATIONS

This application is a continuation of U.S. patent application Ser. No. 10/897,352, filed Jul. 22, 2004, issued as U.S. Pat. No. 7,208,007, which claims priority under 35 U.S.C. 119(e) to U.S. Provisional Patent Application Ser. Nos. 60/493,171, filed Aug. 7, 2003, and 60/582,489 filed Jun. 24, 2004, both of which are incorporated herein by reference.

BACKGROUND OF THE INVENTION

The invention relates generally to the generation of a high brightness optical source through use of a fluorescence concentrator system. The source can be used in a variety of applications, including various medical aesthetic procedures.

As an aid in demonstrating the utility of the invention, it is helpful to review some basic optical concepts. For a pulsed optical source the pulse energy is defined as the average optical power during the pulse multiplied by the pulse width. Typical units for pulse energy are Joules, for power are Watts, and for time is seconds. The optical intensity is the power per unit area, typically expressed in units of $W/cm^2$. The optical fluence is defined as the pulse energy incident on a unit area. Typical units are Joules/centimeter$^2$ ($J/cm^2$). The spectral fluence is the pulse fluence per unit of wavelength. Typical units for wavelength are nanometers so the spectral fluence is often expressed in units of $J/(cm^2*nm)$. The brightness of an optical source is the power per unit area per unit solid angle. Typical units are $W/(cm^2*steradian)$. The spectral brightness is the brightness per unit wavelength. Typical units are $W/(cm^2*steradian*nm)$. Brightness and spectral brightness are also known by the terms radiance and spectral radiance.

It is a well-known axiom of optics that the brightness or spectral brightness of a light source generally cannot be increased by propagating the light through any classical optical system. Such optical systems can, at best, preserve the brightness of an optical source. This brightness constraint limits the ability to increase the intensity or fluence by simply focusing an optical beam. Most types of optical sources have insufficient brightness to deliver the intensity or fluence necessary to perform typical aesthetic medical procedures, such as removal of hair, pigmented lesions, or superficial small blood vessels. Thus, special high brightness sources are typically used to perform medical aesthetic procedures.

There are two optical systems that are known to increase brightness. One well-known system is an optically pumped laser. In laser systems it is easily possible to increase source brightness by factor of 10,000 or more. There are many examples of such laser systems, the most common being a neodymium-doped yttrium aluminum garnet (Nd:YAG) laser pumped by a flashlamp or laser diode. These lasers are often incorporated into medical platforms used in aesthetic procedures, for example the Coolglide Xeo system manufactured by Cutera, Inc., of Brisbane, Calif.

A second, much less well-known technique to increase optical brightness is through use of a fluorescence concentrator. A number of papers from the 1950s and 1960s describe concept of a fluorescence concentrator, and it appears that such discussion was largely in connection with different detection systems, for example see the following references which are incorporated herein by reference, *Radiance Amplification by Multi-Stage Fluorescence System*, W. A. Shurcliff, Journal of the Optical Society of America, Vol. 41, No. 3, p. 209 (1951); *The Collection of Light from Scintillation Counters*, Richard Garwin, Review of Scientific Instruments, Vol. 31, p 1010, (1961); *Radiance Amplification by Fluorescence Radiation Converter*, Gunter Keil, Journal of Applied Physics, Vol. 40, p. 3544 (1969).

Fluorescence concentrators guide some fraction of fluorescent light isotropically generated in a body by total internal reflection within the body. The body can be a solid material containing a fluorophore. The guided fluorescent light emerges from an output surface of the body, where the output surface could be one or more ends of the body. The cross-sectional area of the end or ends is typically small compared to the total surface area of the solid. The emerging fluorescent light can have a brightness exceeding that of the original illumination source. The fluorescence concentrators can be arranged serially so that one concentrator pumps a subsequent concentrator, further amplifying the brightness.

Currently fluorescence concentrators are found in a number of commercial systems. One application is as a particle detector in high-energy physics. In this sensor application the illumination source consists of high-energy particles from nuclear interactions. Energy from these particles is partially converted to near-ultraviolet or visible light by a fluorophore contained within an optical fiber. A fraction of the emitted light is transmitted to the fiber end where it is detected by a photomultiplier tube or photodiode. Suppliers for these types of fluorophore doped plastic fibers are Bicron, a division of Saint Gobain, of Newbury, Ohio and Optectron Industries of Les Ulis Cedex, France.

There has been at least one attempt to use a fluorescence concentrator system as an illumination source for an emergency light source. The pump source was a phosphorescent material surrounding a fluorescence concentrator. Such a system was described by Mitsunori Saito & Kazauya Yamamoto, in an article entitled, Bright Afterglow Illuminator Made of Phosphorescent Material and Fluorescent Fibers, found in Applied Optics, Vol. 39, p 4366 (2000). The brightness provided by this source was less than that provided by conventional fluorescent and incandescent lamps. The maximum reported output intensity was slightly less that $100\ nW/mm^2$ or $10\ \mu W/cm^2$.

As discussed herein one fluorescence concentrator includes a transparent host material containing the fluorophore, the host material forms a geometric solid body within which the fluorophore is contained. This body may be homogenous or may have some internal structure, as will be discussed in more detail below.

A wide variety of light therapies have been developed over the last few decades to treat a number of medical conditions. Several of these therapies make use of light energy for treatment of dermatological conditions, improving the aesthetic appearance of the treated dermis and epidermis. These therapies typically work by selectively heating a naturally occurring (endogenous) chromophore to an elevated temperature sufficiently high to effect and possibly denature the tissue in the region of the chromophore. The therapies require a minimum light intensity or fluence at the tissue. The light should be delivered in a sufficiently short time for selective photothermolysis to occur. That is, the optical energy needs to be applied in a sufficiently short pulse, so that the heat produced by absorption in the targeted chromophore has insufficient time to conduct away from the absorption volume of the targeted tissue. The heat thus locally raises the chromophore temperature, denaturing, or damaging, the tissue immediately surrounding the chromophore. The targeted tissue can then be absorbed, sloughed, exfoliated over time, or otherwise biologically altered through a wound-healing type response by the surrounding tissue leaving the treated area clear or otherwise altered. Selectivity can be achieved by use of optical wavelengths that are strongly absorbed in the targeted chromophore. Selectivity can also be achieved by directing the light only at tissue areas that contain high concentrations of the targeted chromophore. The non-targeted areas are left undamaged or only slightly damaged by the procedure. If is often desirable to cool the epidermis prior to and/or during and/or after the treatment to minimize thermal injury to the non-targeted areas. To achieve therapeutically useful light levels generally the optical intensity must be in the range of, or exceed, 10 W/cm$^2$. This corresponds to, for example, an optical fluence of 0.2 J/cm$^2$ delivered in a 20 msec pulse (many dermatologic anatomical structures are characterized by sizes corresponding to thermal diffusion or relaxation times on the scale of 1-100 ms, such as hair, pigmented epidermal lesions and small-to-medium size blood vessels.) The required efficacious fluence varies widely depending on the target tissue, target chromophore, treatment size, and desired result.

Hemoglobin and melanin are two naturally occurring chromophores which are often targets in light therapies. For example, telangiectasias, commonly referred to as spider veins, and other subcutaneous vascular conditions, are treated by selectively heating the targeted chromophore, hemoglobin, found in blood vessels, with laser light energy. In this procedure selectivity is achieved by directing the treating light at the readily visible blood vessel. Similarly, selective heating of melanin with laser energy is now widely used for hair removal or epilation, removal of skin lesions, and other conditions where melanin-bearing structures can be targeted. Both of these therapies may be performed, using a optically-pumped Nd:YAG laser having a wavelength of 1,064 nanometers such as that described in issued U.S. Pat. No. 6,383,176, which is incorporated herein by reference. Such laser-based treatments have been widely adopted, and are successfully treating large numbers of patients for a variety of dermatological and other conditions.

Aside from choosing a therapeutic wavelength which is well absorbed by the target chromophore, it is also important to consider the tissue scattering properties and the absorption of non-targeted chromophore. Hemoglobin has a broad absorption peak located between 500 nm and 600 nm. Melanin has a monotonically rising absorption with shorter wavelengths. Thus, short wavelength treatments that target melanin generally require lower intensities to achieve that same therapeutic efficacy as long wavelength treatments. Tissue scattering also increases with shorter wavelengths. Thus to target shallow structures shorter wavelengths can be used, while longer wavelengths can be used for deeper structures.

Medical apparatus used in light therapy treatments typically have a user-directed applicator or handpiece that delivers light to the skin surface. Typical protocols for dermatologic aesthetic treatments usually involve (1) contacting or positioning the applicator so as to direct treatment light at a local region of skin, (2) optionally initiating some type of epidermal cooling (such as contact with a cooled optical window), (3) directing a pulse of optical energy through the applicator to the skin surface for a proscribed duration, (4) repositioning the applicator to a new treatment region of skin, and (5) repeating steps 2 and 3. This general protocol is referred to as a "stamping" modality.

The stamping modality has many variations. The applicator can be used in either a contact or non-contact mode depending on the applicator design, type of treatment, and cooling method used. If contact is used it can be either "hard" contact, where the applicator is pressed into the skin, or "soft" contact, where the applicator lightly touches the skin. In some cases no contact is required such as the method described in pending U.S. Patent Publication No. 2005/0107852, filed Feb. 19, 2004, entitled METHODS AND DEVICES FOR NON-ABLATIVE LASER TREATMENT OF DERMATOLOGIC CONDITIONS which is assigned to the assignee of the present application and which is incorporated herein by reference. For small isolated features, such as a pigmented skin lesion, only a single treatment site may be required for some treatments. It may be desirable to irradiate the same site with multiple pulses. This can be done by making multiple passes over the treatment area or by directing multiple pulses at a single treatment site before repositioning the applicator.

The light source may be configured in a variety of ways as part of the medical apparatus. A laser or other light source may be contained in a separate console and propagated by some means to the applicator. Other apparatus houses the laser or light source inside the applicator device, avoiding the need to propagate the light from a console. It is possible to configure the medical apparatus as part of a medical platform which allows different apparatus to share common platform components. For example, the Coolglide/Xeo medical platform manufactured by Cutera, Inc., of Burlingame, Calif. can be configured with either a flashlamp or laser light source. Such platforms typically include a means for cooling the skin through the applicator or handpiece. For example, U.S. Pat. Nos. 6,383,176 and 6,485,484 describe one type of cooling used with the CoolGlide laser handpiece, and both of these patents are incorporated herein by reference.

While generally successful, existing optically-pumped laser-based treatments still have certain disadvantages. Specifically, known commercial laser therapy systems have often employed large, rather expensive lasers to generate sufficient intensity or fluence for therapeutic efficacy. Many of these lasers require regular maintenance to provide the desired performance. The lasers typically require precise mechanical tolerances and thus cannot readily be serviced. Additionally, existing lasers are often inflexible in the light wavelengths they produce. As different therapies benefit from different optical wavelengths, entirely separate laser systems are often required to perform different therapies. Finally, laser-based therapies are accompanied by a significant eye safety risk. Eye safety is particularly problematic when there are multiple laser wavelengths and pulse parameters used at a medical site and where multiple spectacle styles and optical characteristics for protective eyewear are required.

More recently, alternative therapeutic light sources have been proposed. These alternative light sources include laser diodes, flashlamps, light emitting diodes (LEDs). While these alternative structures can have significant cost advantages over optically-pumped lasers, each has significant disadvantages. When sufficient laser diodes are combined to generate therapeutic light fluences, the total cost of the device is quite high, often in the many thousands of dollars. Moreover, high power laser diodes are only available in a limited number of wavelengths; they are not currently available in wavelengths shorter than approximately 630 nm and thus cannot target the hemoglobin absorption peak near 550 nm. While flashlamps are very low in cost, they have a large emitting volume and low spectral brightness. Reflectors and apertures are typically used to collect, direct and control the flashlamp light to the dermis. The reflectors must be precisely built and calibrated, as errors can produce hot spots in the spatial energy distribution. Furthermore, as the spectrum of light energy generated by lamps is quite broad and much of the total light energy may disadvantageously cause heating of non-target chromophores. This disadvantageous light can be reduced by use of a wavelength selective optical filter. However, the filter is expensive, reduces the fluence of the desired light, and only imperfectly removes the unwanted light. Both direct flashlamp and filtered flashlamp systems produce light of only moderate spectral brightness over a relatively large area and thus cannot produce a spatially localized, high spectral fluence source. LEDs are low in cost and are available at most wavelengths across the visible spectrum. Unfortunately, LEDs typically have insufficient brightness to cause selective photothermolysis of appropriate tissues or structures bearing naturally-occurring (endogenous) chromophores.

There remains a need for a low cost light source of sufficient spectral brightness and spectral fluence to be therapeutically efficacious in treating various dermatological conditions.

DETAILED DESCRIPTION

Figure 1:
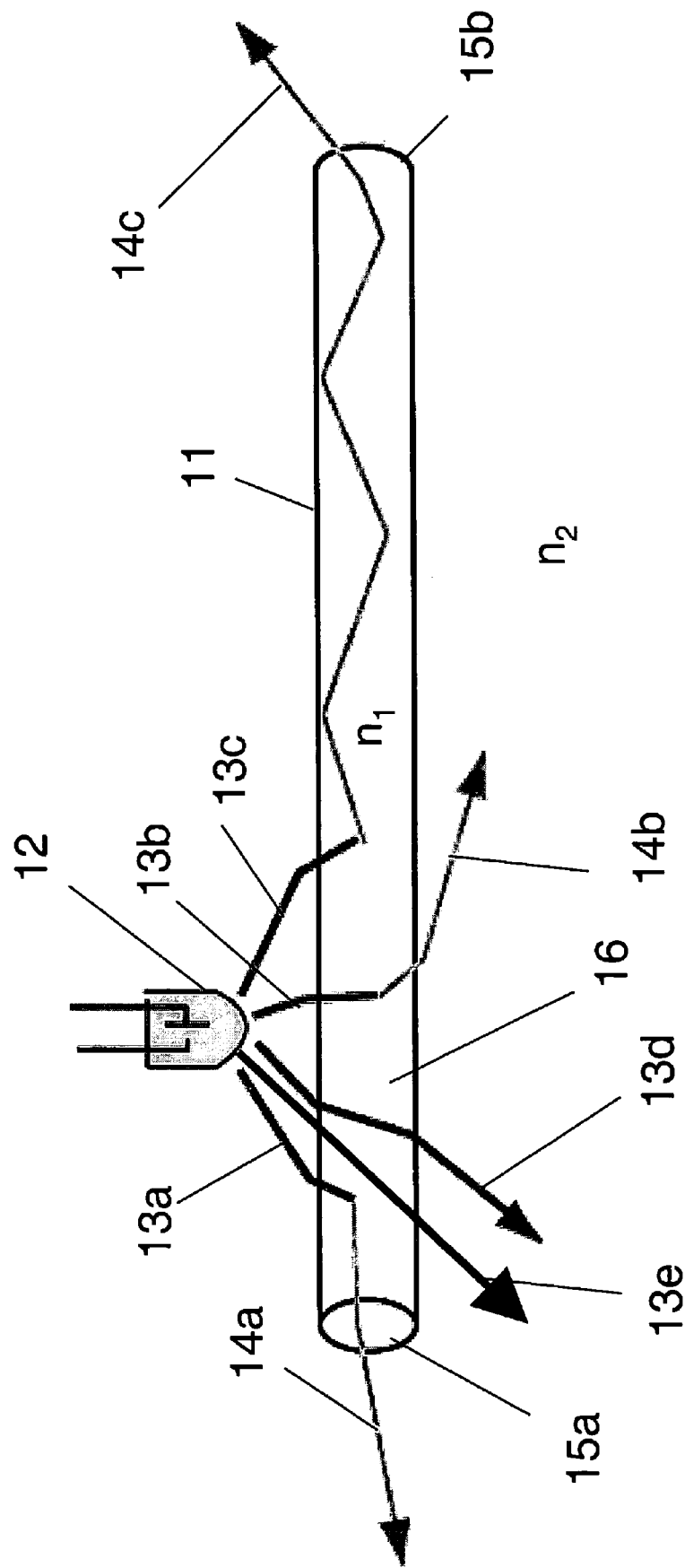
FIG. 1 shows an embodiment a fluorescence concentrator system herein.

One embodiment herein provides a fluorescence concentrator which is capable of producing a high spectral brightness and high intensity optical source suitable for providing therapeutic energy, which can be used for medical procedures.

An embodiment herein provides a system which includes a body with a fluorophore, which can be a transparent optical material doped with a fluorophore to form a fluorescence concentrator. The fluorescent concentrator can be optically smooth at most or all surface boundaries. In one embodiment the material has an index of refraction higher than its surroundings so that total internal reflection (TIR) can occur at the concentrator surfaces. The concentrator has at least one surface for outputting energy. This output area can be significantly smaller than the total surface area of the fluorescence concentrator. The concentrator is illuminated by an adjacent illumination source which optically pumps the fluorophore causing it to emit fluorescent photons. The illumination source can be a flashlamp, LED, or another fluorescence concentrator. The fluorescent photons can have a longer wavelength than the pump photons. Some fraction of the emitted fluorescent photons are guided by the concentrator surfaces and emerge at the output area. The brightness and/or spectral brightness, and/or intensity at the output area can often exceed that of the illumination source.

In one embodiment a fluorescence concentrator system can be incorporated in a medical apparatus. The system output light can be delivered to the treatment area either by placing the output area proximal to, or in contact with, a treatment area or by using an optical delivery system. The optical delivery system could use an optical fiber, a lens, or a series of lenses, or a filter. The medical apparatus can include a means to cool the treatment area, helping to minimize unwanted damage. The apparatus can include drive and control electronics and a user interface.

In one embodiment a system output wavelength is advantageously chosen to overlap the absorption spectrum of naturally occurring chromophores by choice of an appropriate fluorophore, fluorophore concentration, and system geometry. Dimensions of the output area can be chosen to approximately match at least one dimension of the treatment area. Large areas can be treated by successively irradiating adjacent, previously untreated areas, a process sometimes referred to as stamping. The output light is of an appropriate wavelength and of sufficient intensity and fluence to cause the desired therapeutic effect.

Fluorescence concentrator systems can provide advantages in various medical aesthetic procedures that locally denature, or otherwise alter, the tissue surrounding a target chromophore by selective photothermolysis. Examples of such procedures that target hemoglobin include removal of telangiectasias, commonly referred to as spider veins. Procedures that target melanin include removal of pigmented lesions, such as solar lentigines, dyschromia, hyperpigmentation and freckles. Also hair can be permanently removed by locally heating the melanin in the hair follicle, destroying the follicle. In addition to medical treatments that target naturally occurring chromophores a fluorescent concentrator system could be used with other types of chromophores. For example, tattoos can be treated with the output light from a fluorescence concentrator system.

Fluorescence concentrator systems can also be useful as a light source in medical procedures utilizing target chromophores that do not rely on selective photothermolysis for their therapeutic efficacy. Such procedures could induce photochemical changes in endogenous or user supplied (exogenous) chromophores. An example of such a procedure using an exogenous chromophore is photodynamic therapy.

In addition to the medical field, embodiments of the high brightness or high intensity fluorescence concentrators, and fluorescence concentrator systems could be used in any application requiring relatively high optical intensities, such as applications exceeding 10 W/cm$^2$.

An embodiment of the system and method herein provides for a low-cost, light source capable of producing output intensities of greater than 10 W/cm$^2$. Further, systems and methods herein can be used to provide a light source of appropriate wavelength and sufficient intensity to alter target tissue naturally occurring in a target area of a patient's tissue; where the tissue could be a patient's skin which includes both an epidermis layer and an underlying dermis. As will be apparent to one skilled in the art a variety of different treatments, and applications, including providing for a variety of medical aesthetic procedures can be performed using embodiments of the fluorescent concentrator system disclosed herein.

FIG. 1 illustrates the basic physical principles of a fluorescence concentrator system, where the term fluorescence concentrator system generally refers to the fluorescence concentrator, the illumination source used to optically-pump the fluorescence concentrator, and any auxiliary optical materials or surfaces which may be used to increase system efficiency. Fluorescence concentrator 11 is illuminated by adjacent illumination source 12. Fluorescence concentrator 11 includes a body where at least part of the body is doped with a fluorophore. The body will generally be some transparent host. In one embodiment the fluorescence concentrator 11 has two nominally flat end surfaces 15a and 15b and nominally cylindrical side surface 16. In one embodiment all or most surfaces of concentrator 11 are optically smooth. Fluorescence concentrator 11 has a refractive index of $n_1$ on its side surface 16 and is surrounded by a medium of lower refractive index, $n_2$. Fluorescence concentrator 11 has a circular cross-section whose diameter is less substantially less than its length. The possible paths of pump photons are illustrated in FIG. 1. Pump photons 13a, 13b, 13c, and 13d from illumination source 12 enter fluorescence concentrator 11 through side surface 16. Photon 13e is emitted from illumination source 12 in such a direction that it does not strike fluorescence concentrator 11. Photon 13d passes through concentrator 11 without being absorbed. Photons 13a, 13b and 13c are absorbed by fluorophores doped into concentrator 11. The fluorophores isotropically emit fluorescence photons 14a, 14b, and 14c. Fluorescence photons 14a, 14b, and 14c have a longer wavelength than pump photons 13a, 13b, and 13c. Photon 14a is emitted in a direction so that it emerges from output surface 15a without striking side surface 16 of fluorescence concentrator 11. Photon 14b is emitted in a direction such that it emerges through side surface 16 of fluorescence concentrator 11. Photon 14c is emitted in a direction such that it is captured by total internal reflection off side surface 16 and is guided to end surface 15b. The output emission of a fluorescence concentrator system is through end surfaces 15a and 15b. The emission pattern fills the aperture of surfaces 15a and 15b and has a nominally Lambertian angular distribution. Pump photon 13b, which produced a fluorescent photon that is not captured by concentrator 11, pump photon 13d which is not absorbed in concentrator 11, and pump photon 13e which did not strike concentrator 11, did not contribute to the output emerging from surfaces 15a and 15b.

The fraction of emitted fluorescence energy, shown as fluorescence photons 14a, 14b, and 14c, that is captured and guided toward surfaces 15a and 15b in a circular optical fiber ($f_{\rightarrow}$) is approximately given by the expression $f_{\rightarrow}=[1-n_2/n_1]/2$. The term $f_{\rightarrow}$ represents the theoretical single-sided capture efficiency. The capture efficiency is estimated by considering the fraction of on-axis, isotropically emitted fluorescent rays that would have emission angles at or below that required for TIR at the fluorescent concentrator side surface. Table I lists typical theoretical single-sided capture efficiencies for different embodiments of fluorescence concentrator systems.

TABLE I

| System (fluorescence concentrator material/surrounding medium) | Fluorescence concentrator index ($n_1$) | Surrounding medium index ($n_2$) | $f_{\rightarrow}$ |
|---|---|---|---|
| YAG crystal/air | 1.84 | 1 | 0.23 |
| Polystyrene/air | 1.59 | 1 | 0.19 |
| YAG crystal/water | 1.84 | 1.33 | 0.14 |
| Polystyrene/water | 1.59 | 1.33 | 0.082 |

Inspection of Table I indicates that the single-sided capture efficiencies are in the range of 8% to 23%, easily high enough for a useful optical system. A high refractive index medium, for example, YAG, surrounded by water still has a useful capture fraction of 14%.

Various factors influence the efficiency of a fluorescence concentrator system. The pump light from illumination source 12 must be absorbed by concentrator 11, otherwise it is wasted. Methods to increase the absorption efficiency include the use of an illumination source whose emission wavelength overlaps with the fluorophore absorption peak. The fluorophore doping concentration should be chosen so that a significant fraction of pump light 13 is absorbed in a single pass through fluorescence concentrator 11. It is also desirable to close-couple illumination source 12 to fluorescence concentrator 11 by making the separation between them as small as mechanically convenient. A geometry where fluorescence concentrator side surface 16 intersects all emission of illumination source 12 is desirable, since all pump photons impinge on the fluorescent concentrator and none are wasted.

Another factor affecting fluorescence concentrator system efficiency is the fluorophore quantum efficiency. The quantum efficiency is improved by minimizing the Stokes shift between pump photons 13 and emitted photons 14. Also, the branching ratio of the fluorophore should be high, so that most of the absorbed pump photons produce fluorescence in the desired wavelength band. Furthermore, fluorophores with low levels of excited state absorption are desirable.

Self-absorption by the fluorophore of emitted fluorescence light 14 in fluorescence concentrator 11 is a major limitation on system efficiency. Especially in organic dye fluorophores there is significant overlap between absorption and emission wavelengths. This results in a significant fraction of emitted photons 14 being absorbed in fluorescence concentrator 11, since many of the emitted photons must travel long optical paths to reach the ends 15a and 15b. Self-absorption shifts the output emission spectra to wavelengths that are less strongly absorbed in concentrator 11. As a result the output emission spectra is typically red shifted relative to the fluorophore intrinsic emission spectrum. Some of the self-absorbed fluorescent light is not lost, but can be reemitted at longer wavelength. Methods to minimize the effects of self-absorption loss are using fluorophores with large Stokes shifts, decreasing the fluorophore doping concentration, and decreasing the optical path length between the emission point and the end surfaces 15a and 15b.

Other loss mechanisms that reduce the efficiency of a fluorescence concentrator system are scattering within fluorescence concentrator 11, and scattering and absorption from concentrator side surface 16. The scattering loss can be reduced by use of materials of good optical quality and providing an 80/50 or better scratch/dig optical surface finish on fluorescence concentrator side surface 16. Contact between side surface 16 and any support structures should be minimized to reduce scattering and absorption loss at the contact points. Furthermore, contact between side surface 16 and some support structure (not shown in FIG. 1) can destroy the total internal reflection condition required to guide light to end surfaces 15a and 15b.

Some factors that improve one aspect of fluorescence concentrator system efficiency can degrade other aspects of efficiency. In specifying a fluorescence concentrator system capable of delivering a therapeutically efficacious optical fluence various engineering tradeoffs must be made. These tradeoffs are exemplified in the description of a preferred embodiment.

Figure 2:
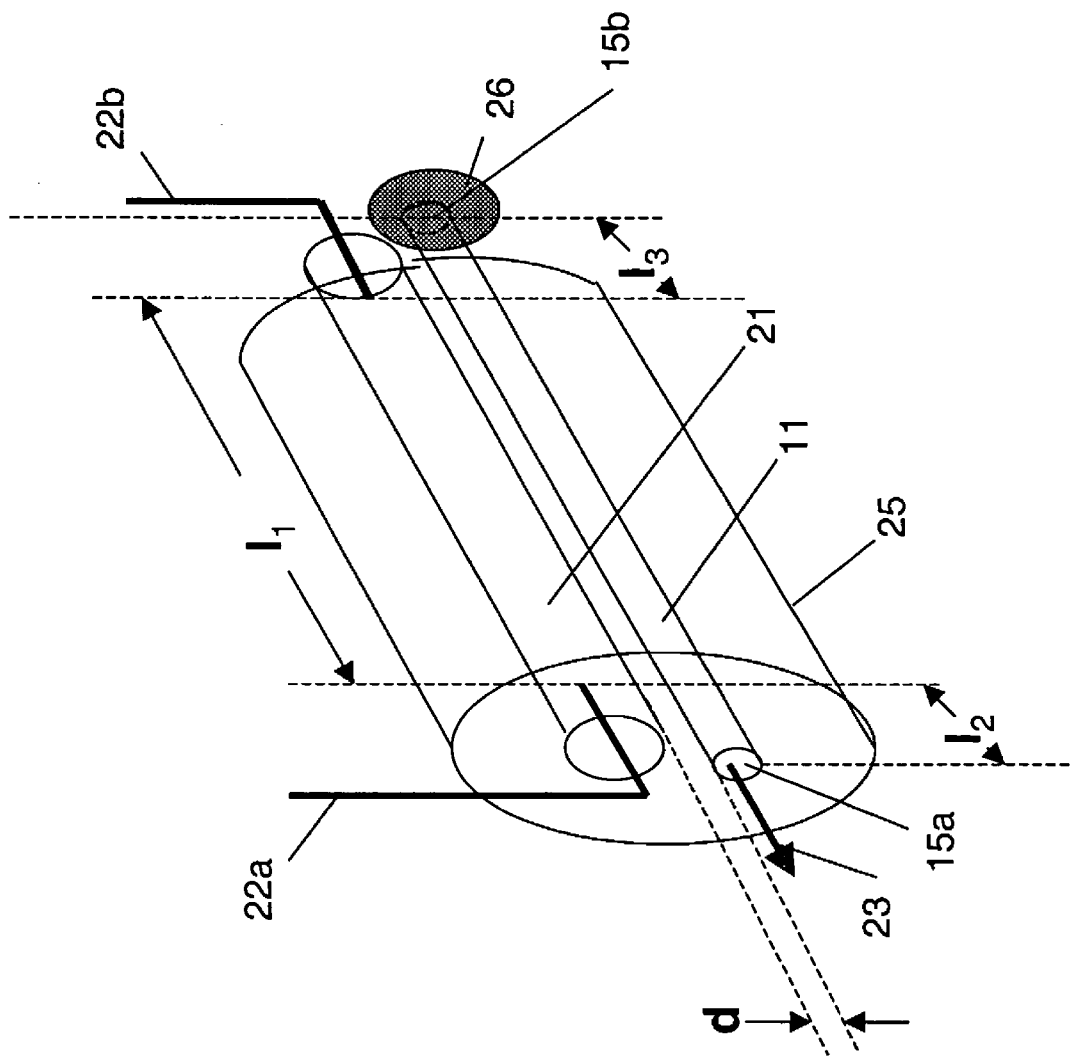
FIG. 2 shows a perspective view of an embodiment of a fluorescence concentrator system herein which uses a flashlamp as the illumination source.

FIG. 2 shows an embodiment of a flashlamp-pumped, fluorescence concentrator system 20 capable of producing therapeutically efficacious optical fluences. Flashlamp 21 is the illumination source and is placed adjacent to fluorescence concentrator 11. The spacing d between flashlamp 21 and fluorescence concentrator 11 is as small as mechanically convenient, typically less than the diameter of fluorescence concentrator 11. Flashlamp 21 has an emission length $l_1$, which corresponds to the arc length of flashlamp 21. Fluorescence concentrator 11 consists of a fluorophore doped into a body, which is typically a transparent host. Substantially all outer surfaces of concentrator 11 are optically smooth. The output surface 15a is less than 1/10 the total surface area of concentrator 11. Length of fluorescence concentrator 11 is chosen so that it is approximately equals or minimally exceeds the length of flashlamp 21. The length of concentrator 11 which is not adjacent to the emission length of flashlamp 21 ($l_2$ and $l_3$) is minimized. The medium surrounding concentrator 11 has a lower refractive index than concentrator side surface 16. Reflective structure 25 substantially surrounds fluorescence concentrator 11 and flashlamp 21 and is made as close fitting as mechanically convenient. This reflective structure can also form, or be incorporated into, a housing for the fluorescent concentrator system. Reflective surface 26 is placed proximal or in direct contact with one of the fluorescence concentrator ends 15b. Support structures for concentrator 11 and flashlamp 21 typically attach at the ends of reflective structure 25, and form a mounting system. In one embodiment the mounting system for concentrator 11 can allow the fluorescent concentrator body to be easily removed, and replaced with another concentrator. This allows a user to easily switch concentrator bodies to obtain different spectral characteristics or geometric characteristics, or to replace a concentrator when its performance has degraded. The support structure makes only minimal contact with concentrator 11, especially near end 15a which provides an output area. The fluorescence concentrator 11 could also be supported all or in part by reflective surface 26. Reflective surface 26 is in turn attached to reflective structure 25 by some support structure.

Flashlamp 21 is a moderately bright, intrinsically pulsed illumination source. Power to flashlamp 21 flows through flashlamp electrical leads 22a and 22b. The drive and control electronics (not shown in FIG. 2) are capable of generating several hundred volts. As will be appreciated, a variety of different power supplies could be used. In one embodiment electrical energy is stored in one or more capacitors (not shown) and flows through flashlamp electrical leads 22a and 22b when breakdown in the flashlamp has been initiated by a high voltage, low energy trigger pulse. In one embodiment currents flowing through flashlamp 21 during the discharge can easily exceed 100 amperes. The discharge pulse width is determined by the capacitance, inductance, resistance, and drive voltage used in the drive and control electronics. Longer pulse widths can be generated by increasing the inductance and resistance in the circuit. Shorter pulse widths can be generated by increasing the drive voltage. Depending on the desired output pulse width and energy of fluorescence concentrator system 20, flashlamp 21 drive voltages can range from 300 V to 10 KV and the storage capacitor can have capacitance values in the range of 100 microfarad to 5,000 microfarad.

During the discharge flashlamp 21 emits photons (not shown in FIG. 2), some of which are in the absorption band of fluorophore doped fluorescence concentrator 11. The fluorophore absorbs some of the pump light producing fluorescence photons. Output light 23 is produced by the fluorescence photons which emerge from end 15a which provides an output area. A reflective structure 25 around fluorescence concentrator 11 and flashlamp 21 redirects pump photons that may have initially missed or passed through concentrator 11 back to the concentrator where they may be absorbed by the fluorophore. Reflective surface 26 redirects fluorescent photons toward end 15a improving efficiency.

Many different types of fluorophores can be used in fluorescence concentrator 11. Organic fluorescent dyes offer essentially a continuous span of emission wavelengths across the near ultraviolet, visible, and near-infrared spectrum. Various inorganic ions such as, but not limited to, Ce, Er, Pr, Ho, Dy, U, and Tb possess emission spectra and quantum efficiencies that may make them attractive fluorophores. A new type of fluorescent material, quantum dots, which are engineered nanoparticles, offer broad absorption bands in the visible and ultraviolet coupled with excellent quantum efficiency. Quantum dots dissolved in a liquid or doped into a polymer matrix are available from Evident Technologies of Troy, N.Y.

Many types of transparent host materials can be used in fluorescence concentrator 11. An attractive low-cost option is use of a plastic such as polymethyl methacrylate (PMMA), polystyrene, or various high refractive index plastics such as Optindex available from Brewster Science of Rolla, Mo. A high temperature plastic such as Excilite™ developed by Korry Electronics of Seattle, Wash. and referenced in U.S. Pat. No. 5,805,623 is another potential polymer host material. Liquids may also be used as the fluorophore host. Typical liquids would be similar to those used in liquid dye lasers. Glasses, either conventionally processes, or fabricated via a sol-gel process are also attractive host materials. Kigre Inc., of Hilton Head, N.C. offers a terbium-doped glass (part #JL-27) which is an attractive choice for a fluorescence concentrator material. In addition single crystals such as, but not limited to, YAG, sapphire, and lithium niobate may be advantageously used. Likewise transparent ceramics, such as transparent YAG ceramic available from Baikowski International Corporation of Charlotte, N.C. may be advantageously used.

Table II summarizes the approximate peak emission wavelengths obtained from various fluorescence concentrator materials. The same fluorescence concentrator material can emit at slightly different peak wavelengths depending on the system geometry, dopant concentration, and pump source. The wavelengths listed in Table II span the visible spectrum from violet to red wavelengths. The materials listed in Table II do not represent a comprehensive listing, but they do demonstrate the wavelength flexibility available in fluorescence concentrator systems. Materials emitting at both shorter and longer wavelengths, as well as other materials in the visible wavelength range, are available.

| Fluorescence Concentrator Material | Approximate Peak Emission Wavelength (nm) |
|---|---|
| Optectron Industries # F2001000 | 428 |
| Optectron Industries # F2011000 | 499 |
| Bicron #693-00001 | 512 |
| Kigre #JL-27, Terbium doped glass | 542 |
| Cerium doped YAG (0.5% Ce) | 548 |
| Optectron Industries # F2032000 | 555 |
| Bicron #69906A-00001 | 580 |
| Optectron Industries # F2041000 | 630 |

Various practical considerations go into the design of fluorescence concentrator system 20. An important consideration is the shape and dimensions of fluorescence concentrator 11. In one embodiment to increase brightness, the output surface area at end 15a should be less than 1/10 of the total surface area of concentrator 11. Typically a thin rod, fiber or elongated plate is the preferred shape. The cross-section can be circular, square, rectangular, or other shape. The length of concentrator 11 which is not adjacent to emission length of flashlamp 21 ($l_2$ and $l_3$) should be minimized to reduce self-absorption losses in these regions. The length of concentrator 11 should also not be significantly greater than the concentrator attenuation coefficient at the emitted fluorescence wavelength. For typical fluorophore/host combinations this limits the practical concentrator maximum dimension to lengths shorter than 1 meter. In one embodiment the minimum cross-sectional dimension of concentrator 11 should be comparable to the absorption depth at the peak of the fluorophore absorption spectrum. The absorption depth is controlled by the doping level and is typically on the order of a cross-sectional dimension of the concentrator. In one embodiment of a concentrator, a diameter for a cross-sectional area of the concentrator, could be in the range of 0.5 mm to 6 mm, of course depending on different applications one might use a different concentrator having a different diameter.

Fluorescence concentrator 11 may be fabricated from a homogenous material or may have a thin, transparent, low-refractive-index cladding around a higher-refractive-index, fluorophore doped core. The fluorescence concentrator 11 shown in FIG. 1 for example, could be homogenous material. Alternatively, a lower refractive-index cladding could be disposed around a higher refractive index inner core material. Examples of properties of such a structure are discussed in more detail below in connection with Table II. The embodiment using a cladding layer is similar to the design of optical fibers and helps to reduce absorption and scattering losses at side surface 16. Fluorescence concentrator system 20 can advantageously use this same principle. In this case some optical guiding by total internal reflection at the core/clad interface will occur. This interface is optically isolated from its surrounding by the cladding, allowing the guiding to be independent of the local environment. As such, the guiding is not influenced by contamination or mechanical damage on concentrator side surface 16. The clad thickness is small compared to the core thickness, since the clad need only be several micrometers thick. In the case of a clad fiber, optical guiding will typically occur at both the core/clad interface and the clad/surrounding medium interface. In most cases the majority of the captured light is guided by the clad/surrounding medium interface, since the index difference between the materials at that interface is larger. Values for the single-sided capture fraction for typical fluorescence concentrator system configurations are listed in Table III.

TABLE III

Single-sided capture fraction at various interfaces

| System (core/cladding) | High refractive index | Low refractive index | $f_>$ |
|---|---|---|---|
| Polystyrene/PMMA | 1.59 | 1.49 | 0.031 |
| PMMA/water | 1.49 | 1.33 | 0.054 |
| PMMA/air | 1.49 | 1 | 0.16 |
| SiO2 fluorinated SiO2 | 1.45 | 1.41 | 0.014 |

Inspection of Table III indicates that the capture fraction at the core/clad interface is in the range of 3.1% to 1.4% whereas the capture fraction at the clad/surrounding-medium interface is in the range of 16% to 5.4%. One advantageous attribute of light captured by the core/clad interface is that it has lower divergence at output surface 15a compared to light captured at the clad/surrounding-medium interface.

In addition to radial variations in composition, concentrator 11 can also have axial variations. In one embodiment, concentrator 11 has fluorophore present only in the length $l_1$. Concentrator lengths $l_2$ and $l_3$ have can have no fluorophore or lower fluorophore concentrations. This concentrator configuration lowers self-absorption and improves efficiency.

For efficient operation the majority of the emitted pump light must coupled into fluorescence concentrator 11. Long thin illumination sources, such as linear flashlamp 21, are well suited to efficiently couple to rod or fiber shaped fluorescence concentrators. In one embodiment the pumping configuration has a reflective structure 25 surrounding fluorescence concentrator 11 and flashlamp 21 creating a pump cavity. Reflective structure 25 allows increased coupling of pump photons into fluorescence concentrator 11, since all pump photons need not be absorbed in the first pass through concentrator 11 and reflective structure 25 can redirect photons that otherwise would not strike concentrator 11. Reflective structure 25 may be comprised of a specular reflector of aluminum, enhanced silver, or some other material or a diffuse reflector made from $TiO_2$ or $BaSO_4$ particles, ceramic, or some other diffuse material.

In operation much of the input electrical energy which drives the light source is converted to heat. Thus, one embodiment provides for removing some of the heat to avoid damage to fluorescence concentrator 11 and flashlamp 21. For low average power operation heat removal by natural convection to the surrounding environment may be sufficient. This will require sufficient thermal capacitance in system 20 to avoid overheating any components. The thermal capacitance can be increased by surrounding flashlamp 21 and fluorescence concentrator 11 in a liquid, such as water. The thermal capacitance can also be increased by using larger components, having more thermal mass. For example, a larger flashlamp can be utilized operating at pulse energies below its rated value. Another method to improve the thermal performance of system 20 is use of a glass, crystal, or ceramic host instead of a plastic host in fluorescence concentrator 11. The former materials have a much higher operating service temperature and can operate with less aggressive cooling or at higher average power.

For higher average power operation more aggressive heat removal methods may be required. Flowing water or flowing gas can surround either flashlamp 21 or fluorescence concentrator 11, or both components. The water or gas could be cooled prior to contacting system components, for example, by passing the gas through an expansion valve or the water through a heat exchanger. If water is in direct contact with fluorescence concentrator 11 it is advantageous to use a high index material for concentrator 11 to maintain a sufficiently high capture fraction.

One embodiment of a system herein is a fluorescence concentrator system according to the description given in FIG. 2. Flashlamp 21 has an arc length $l_1$ in the range of 80 mm and an outer diameter in the range of 5 mm. Fluorescence concentrator 11 has a length in the range of 123 mm and a diameter of in the range of 1 mm. For such an embodiment the ratio output surface area 15a to the side surface area is approximately 1 to 500. The fluorescence concentrator can be fabricated by polishing both end faces of fluorescent fiber # 693-00001 available from Bicron Inc., of Newbury, Ohio. Fluorescence concentrator 11 has a fluorophore-doped, polystyrene core with a PMMA clad. A small metal mirror can be used as reflective surface 26 by placing it adjacent to end 15b. Reflective structure 25 can be fabricated from aluminum and has a polished tube with an 8 mm inner diameter. The tube inner surfaces can be coated with a thin layer of $BaSO_4$, forming a high efficiency diffuse reflector. End caps (not shown) fabricated from acetal homopolymer can be provided with small clearance holes which support flashlamp 21 and fluorescence concentrator 11. Aside from providing mechanical support the end caps can also serve to reflect pump light back toward fluorescence concentrator 11. The medium surrounding fluorescence concentrator 11 can be air.

In one embodiment the flashlamp 21 is energized by a drive circuit using 380 V of drive voltage and 1200 µF of capacitance which supplies 86 Joules of electrical energy to flashlamp 21. The circuit can produce a 500 µsec long pulse. Output light 23 pulse energy under these conditions is approximately 130 mJ, corresponding to an intensity of 33 $KW/cm^2$ and a fluence of 17 $J/cm^2$. The fluence of fluorescence concentrator light output 23 at the output surface of end 15a is greater than the fluence of flashlamp 21 at the lamp outer wall by a factor of approximately 5.

Figure 3:
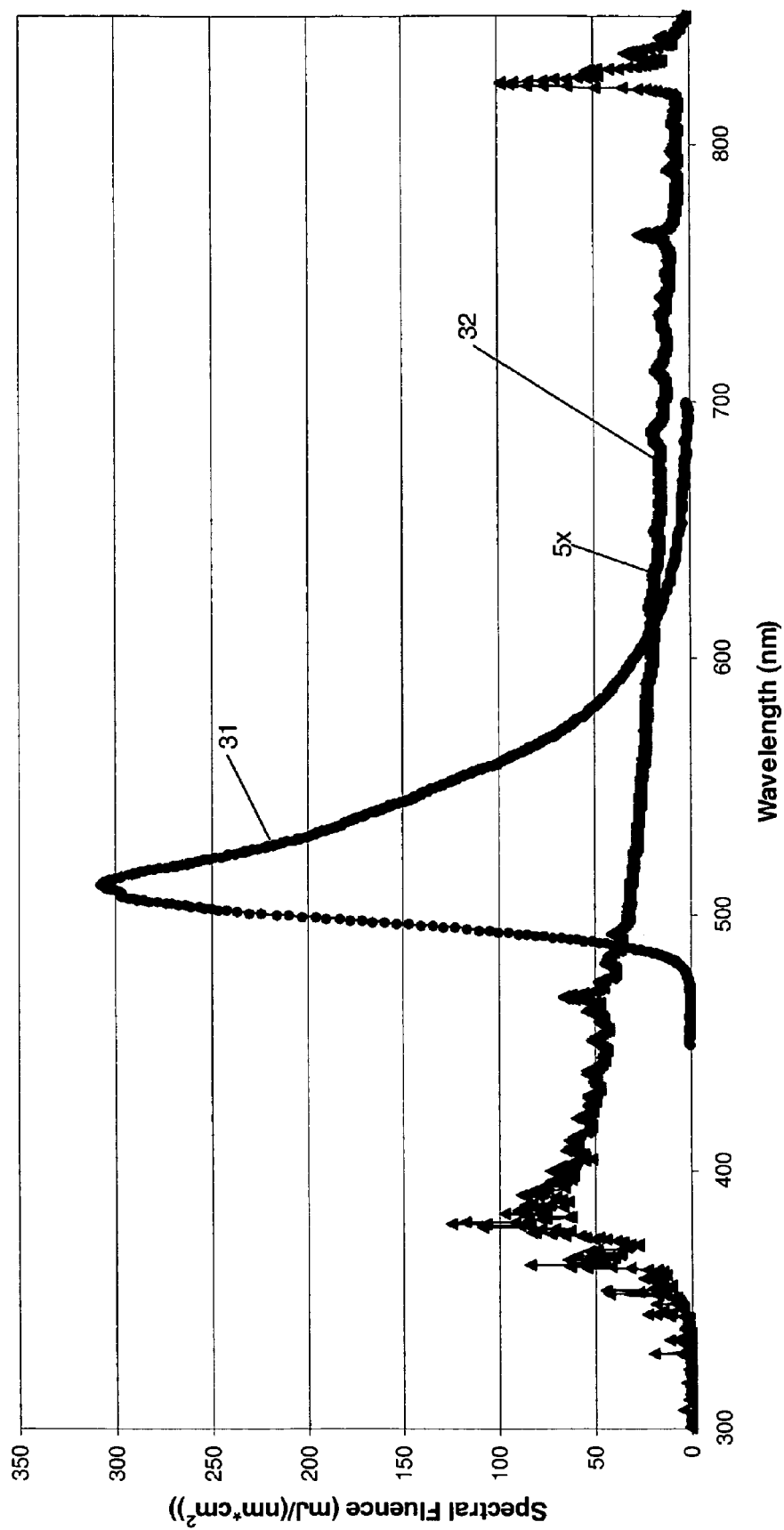
FIG. 3 shows the spectral fluence of an embodiment herein of a fluorescence concentrator system using an organic fluorophore and plastic host material.

FIG. 3 shows the spectral fluence 31 of fluorescence concentrator system 20 during this test. For comparison spectral fluence 32 of flashlamp 21 is also shown in FIG. 3. For clarity the displayed value of flashlamp spectral fluence 32 is 5 times that of the actual value. The maximum spectral fluence of fluorescence concentrator system 20 is approximately 50 times that of flashlamp 21. Across the entire 500 nm to 600 nm spectral window, corresponding to the hemoglobin absorption peak, the fluorescence concentrator spectral fluence 31 is larger than the flashlamp spectral fluence 32.

Additional embodiments of fluorescence concentrator system 20 shown in FIG. 2 are possible. Rather than using a single flashlamp 21 multiple flashlamps could be used to illuminate a single concentrator 11. One example of an additional embodiment would provide for a second linear flashlamp disposed on the other side of the fluorescence concentrator. Further, in another embodiment, instead of a linear flashlamp a helical flashlamp could be used with concentrator 11. In this case concentrator 11 would be positioned within the flashlamp coils. In another embodiment an optical filter could be placed on, or proximal to, output surface 15a of fluorescence concentrator 11 to remove unwanted portions of the output spectral distribution.

Figure 4:
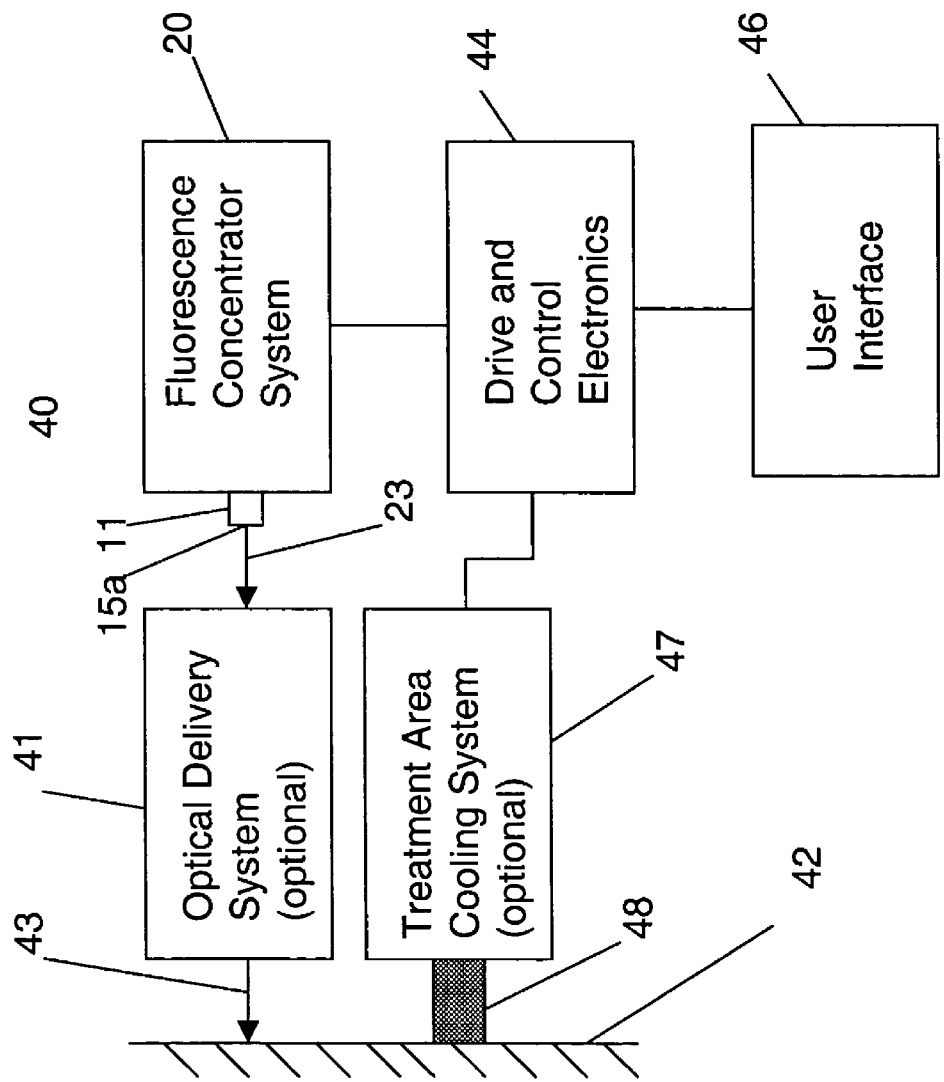
FIG. 4 shows a block diagram of an embodiment of a medical apparatus herein incorporating a fluorescence concentrator system.

FIG. 4 shows a block diagram of an embodiment of a fluorescence concentrator system 20 incorporated into a medical apparatus 40. Several different methods may be used to transport fluorescence concentrator output light 23 to treatment area 42 of a patient's tissue. The simplest method is direct delivery through fluorescence concentrator output area of end surface 15a without use of optional optical delivery system 41. Direct delivery is achieved by positioning surface 15a on, or proximal to, a selected treatment area 42 of a patient's tissue. Thus, where the optical energy is transferred from the output area of the concentrator to the treatment area directly, the optical energy from the output area is therapeutic optical energy to provide the desired treatment to selected area of tissue which alters some characteristics of the tissue. In another embodiment, as shown in FIG. 4, an optical delivery system 41 is used transmit optical energy 23 from the output area to treatment area 42. In this case, therapeutic optical energy or light 43 emerges from optical delivery system 41 and is incident on the treatment area. An optical fiber can form optical delivery system 41 by affixing an optical fiber to concentrator end surface 15a. The optical fiber can have a core size that approximately matches the area of surface 15a. In one embodiment the numerical aperture of the optical fiber should be as large as possible to maximize transmission of output light 23. A plastic optical fiber or transparent plastic rod is a good option. It is advantageous to use an index matching fluid/gel or fuse the joint to minimize losses at this junction. As a further alternative, optical delivery system 41 may use a lens or series of lenses, a window, and/or a filter that deliver output light 23 from the output area of the end surface 15a to treatment region 42.

Fluorescence concentrator system 20 is supplied electrical power and controlled by drive and control electronics 44 which could include a power supply. The electrical parameters supplied by power supply, and other operating parameters of the system, can be controlled by a processor which would be included in the control electronics. In one embodiment a user drive interface 46 is provided. User interface 46 can also provide input for control of an optional treatment area cooling system 47. Cooling system 47 actively cools contact block 48, which makes contact with treatment area 42. Contact block 48 is positioned either adjacent to therapeutic light 43 or therapeutic light 43 may be directed through transparent contact block 48 to treatment area 42. Some contacting fluid or gel (not shown in FIG. 4) can be used to ensure good thermal contact between contact block 48 and treatment area 42.

In situations where the optical delivery system 41, or the fluorescence concentrator end surface 15a, contact treatment area 42, cooling to treatment area 42 can be through these components rather than through a separate contact block 48. A liquid or gel could be used between treatment area 42 and end 15a, or optical delivery system 41, to improve the heat transfer characteristics. Use of a liquid or gel in this region also can increase coupling of therapeutic light 43 into treatment area 42 by serving as an index matching material. The index matching material reduces reflections from end surface 15a or optical delivery system 41, thus increasing transmission. Ultrasonic transmission gel can be used as both the thermal coupling and index matching material.

The fluorescence concentrator system 20, control and drive electronics 44, and user interface 46 and optional optical delivery system 41 and treatment area cooling system 47 could be configured as a stand alone apparatus. The entire apparatus could have the size and general appearance of a single-use camera, since the control and drive electronics 44 could be similar to that found in a single-use camera. Electrical power to the apparatus could be provided by batteries or by plugging the apparatus into a standard wall electrical outlet. In such an embodiment a housing could be provided which houses all of the components of the system. The housing could be formed of molded plastic or metal for example.

The user interface 46 could be very simple, such as simply an on/off switch, or could have some adjustable control parameters, such as pulse energy and pulse repetition rate.

In another embodiment a console could be provide with the control and drive electronics 44 and user interface 46, and a separate housing could be provided with the fluorescent concentrator system 20 and optional optical delivery system 41 and treatment area cooling system 47. The latter components would be mounted in an applicator or handpiece, which is used to direct therapeutic optical energy to a treatment area.

As a further alternative, the medical apparatus 40 or some parts thereof could be incorporated as an accessory or option as part of a larger medical platform. For example, a console with a controllable power supply, user interface, and the ability to control and operate numerous optical energy sources can include the fluorescence concentrator system. One such integrated console is describe in detail in the U.S. pending Publication No. 2005/0137655 filed Feb. 27, 2004, entitled SYSTEM AND METHOD FOR FLEXIBLE ARCHITECTURE FOR DERMATOLOGIC TREATMENTS UTILIZING MULTIPLE LIGHT SOURCES, which is assigned to the assignee of the present application, and is incorporated herein by reference. A commercial embodiment of an integrated console along these lines is the Coolglide/Xeo platform manufactured by Cutera of Burlingame, Calif. which could be advantageously configured to have a fluorescence concentrator handpiece that runs off the main console. In one embodiment most of the drive electronics and control electronics 44, where the drive electronics includes a controllable power supply and the control electronics includes a processor, and user interface 46 are incorporated in the platform console. A computer driven touch screen incorporated in the console provides user interface 46. Fluorescence concentrator system 20 could also use a treatment area cooling system 47 present in the platform. Further, details regarding a system which provides for use of an array of different treatment devices using a counsel which includes a versatile power supply, computer driven touch screen and processor control of the operation of different components of the system is described in the U.S. Patent Publication No. 2005/0137655, which is referred to in more detail above.

A platform using fluorescence concentrators systems as the therapeutic optical energy source provides excellent user flexibility. Different hand pieces could use different fluorescence concentrator systems. Thus an array of different handpieces with different output characteristics would be available. This allows the user to configure the platform for different output spectrum. Alternatively, a single handpiece incorporating fluorescent concentrator system 20 could be configured so that different types of fluorescence concentrator 11 could be installed in system 20. This would enable a single handpiece to provide different output spectra, by changing the fluorescence concentrator. Finally, providing a fluorescent concentrator system where a user can easily replace disposable fluorescent concentrators has great utility. Single use sterile or clean patient contacting fluorescent rods which would be the body of the fluorescent concentrator could be used for a single procedure. Significant amounts of photobleaching or other types of optical or thermal damage to the fluorescent concentrator during use are tolerable if a disposable or replaceable design is used.

Medical apparatus 40 employing fluorescence concentrator system 20 can be used in various medical procedures, especially those that require a spatially-localized, high spectral fluence source. For example in one embodiment, in operation therapeutic light 43 is directed to treatment area 42 by the user. Treatment area 42 contains some unwanted feature or features that selectively absorb therapeutic light 43. Control parameters are set through user interface 46 such that therapeutically useful fluences are delivered. Such doses have sufficient fluence, delivered in a sufficiently short time, to cause photothermolysis. If the unwanted features in treatment area 42 are smaller or equal in size to the spot size of therapeutic light 43, then a single dose of optical radiation may be sufficient. If the unwanted features in treatment area 42 are larger than the spot size of therapeutic light 43, then the user can reposition output 43 so that with multiple shots or pulses from the system, the selected treatment area 42 will be completely irradiated. Treatment area cooling system 47 and contact block 48 can be optionally used to cool treatment area 42. The typical pulse frequency of apparatus 40 is 1 Hz or slower, which gives the user time to reposition therapeutic light 43 between successive pulses. Indeed, in one embodiment the user interface with allow the user of the system to select the pulse frequency from a range of pulse frequencies.

One example of a medical aesthetic procedure where medical apparatus can be advantageously used is removal of small superficial vessels and/or small pigmented lesions. These unwanted features are readily observed by direct visualization. Removal proceeds by (1) positioning the applicator so as to direct therapeutic light 43 at an unwanted feature in treatment area 42, (2) optionally initiating some type of epidermal cooling using contact block 48 or some other means (3) directing a pulse of optical energy through the applicator to treatment area 42 for a proscribed duration, (4) repositioning the applicator to a new treatment area 42 by direct visualization, and (5) repeating steps 2 and 3. In the case of an apparatus 40 that does not use an optical delivery system 41, treatment proceeds simply by placing output area of the of the fluorescence concentrator in contact or near contact with the treatment area 42 and setting user interface 46 to produce a single optical pulse. For removal of pigmented lesions hard contact is used, while for removal of vessels soft or near contact can used.

In these procedures the size of the unwanted feature can be small in at least one dimension, often less than 2 mm. The pulse energy required for efficacious treatment is thus also small, as is the required epidermal cooling. The cooling may be achieved simply through the use of optical coupling gel coupling heat to a passively cooled applicator. More aggressive cooling may be achieved by actively cooling concentrator 11, optional optical delivery system 41, optional contact block 48, or some combination of these components. An attractive configuration, which uses contact of surface 15*a* with treatment area 42, is use of a crystalline host concentrator, such as YAG or sapphire. These materials are mechanically robust, have high thermal conductively, and can be readily cooled with flowing water.

In the treatment of small pigmented lesions, often containing locally high melanin concentrations, treatment is performed by simply treating the entire area of pigmentation. Strong optical contact is advantageous for these treatments, so as to affect pigment and/or melanin at greater depths. A wide range of optical wavelengths may be used as therapeutic light 43, with shorter, blue wavelengths being most strongly absorbed in melanin. It may be advantageous to have a variety of fluorescence concentrator systems from the deep blue (~400 nm) to the red spectral region. The short wavelength systems could be used to treat very light skin types and/or low contrast pigmented lesions. At the other extreme, dark skin types and/or high contrast lesions may be treated with weaker absorbing yellow-green, orange, or red wavelengths.

In the treatment of small vascular structures, such as superficial vessels and telangiactasias, treatment is performed by "tracing" out individual vessels, following along a vessel and exposing the entire length of the vessel using a stamping modality. These treatments typically use near or soft contact, as strong contact will force out blood from treatment area 42 reducing the amount of chromophore present. Wavelengths in the green and/or yellow are typically used since they overlap well with the hemoglobin absorption peak.

Apparatus 40 could also be used for tattoo removal. In treatments for tattoo removal, treatment proceeds as in the case of pigmented lesions. Each type of pigment may be targeted by a fluorescence concentrator system 20 operating at wavelengths corresponding to the pigment peak absorption. Lasers used for tattoo removal are also selected on the basis of matching absorption peaks to laser wavelengths, but in the case of fluorescence concentrator systems, a much wider range of wavelengths are available. The treatment of particularly troublesome tattoo inks, such as yellow or orange, may be advantageously treated by a fluorescence concentrator system using emission wavelengths optimized by the absorption characteristics of yellow or orange inks. Strong optical contact is advantageous for these treatments, so as to affect pigment at greater depths.

Since end surface 15a or optical delivery system 41 can be free from surrounding housings, an unwanted feature can be readily visualized and targeted. Particularly with small lesions or unwanted features prior art systems often obscured treatment area 42. Systems using large spot size laser beams typically have obscuring lens and mechanical support structures in the applicator housing. Flashlamp-based systems frequently include bulky, unwieldy housings which treat large areas and are very difficult to localize to a small region.

During usage some components in fluorescence concentrator system may experience degradation, particularly the flashlamp (or other possible illumination source) or fluorescence concentrator 11. Flashlamps used in photography often have useful lifetimes of approximately 1000 shots. An organic dye fluorophore of the fluorescence concentrator can experience photobleaching from the pump light. Depending on the system power level and configuration, the organic dye lifetime could vary from a single shot to millions of shots. A practical system will typically produce at least 10, preferably several hundred, shots prior to replacing any components. The degraded components, flashlamp 21 and/or fluorescence concentrator 11 can be low cost, probably less than ten dollars each. Fluorescence concentrator system 20 can be designed so that the degraded component is easily replaceable. These replacements could be performed by the end user, since there are no precision alignments required in fluorescence concentrator system 20.

In one embodiment of a system herein as shown in FIG. 2, Bicron fluorescent fiber #693-00001 can be used as fluorescence concentrator 11 the coagulation of blood in a small capillary tube occurs with output pulse energies in the range of 50 mJ, with a corresponding fluence in the range of 6.5 $J/cm^2$. This operation of such a system has shown the efficacy of this system in therapies that utilize hemoglobin absorption, for example, removal of telangiectasias. In addition the same fluorescence concentrator system 20 can be used for targeting melanin. The system can be used to remove solar lentigines, or sun spots, from sun exposed area of skin. For example, in one application a single shot with 80 mJ of pulse energy (corresponding to a fluence of 10 $J/cm^2$) was sufficient to cause photothermolysis in a solar lentigino. The tissue damage was visually equivalent to damage induced with prior art laser or flashlamp systems. Approximately two weeks after treatment the affected tissue naturally exfoliated leaving behind normally pigmented skin.

Generally, the types of epidermal structures amenable to photoselective thermolysis using a small spot fluorescent concentrator are localized, superficial and small in size. These include "freckles", solar lentigines, cherry hemangiomas, telangiectasias or other small superficial vessels. A method of one embodiment herein is described below, but it should be recognized that a range of variations is possible.

In one method an area of tissue to be treated is initially visually identified. For example, this may include a user identifying a freckle, or other feature in the skin to be removed. In one embodiment where the system is designed to allow for a user removal and replacement of the fluorescent concentrator body, a user could select a body based on the shape of the output surface. A fluorescent concentrator system can be designed to allow a user to select between different fluorescent concentrator bodies having a range of different spot area geometries and sizes. The size, geometry and location of the targeted structure can be used to determine the choice of spot size. Typical values range between 1 and 4 mm diameter circular spots. Spots may also be square, rectangular, or chosen to be of arbitrary shape. In another embodiment of the system, multiple fluorescent concentrator system could be provided, and a used could select the system having an output shape which most closely corresponds to the feature which is to be treated.

The fluorescent concentrator system can also be implemented to allow a user to select between a range of output light spectral bands, which allows a user to select a correct wavelength for a desired treatment. Generally, the spectral output is determined by the pump source and fluorophore, and possible filtering, and will not be tunable. Manually or optomechanically changing a filter, or the fluorescent concentrator body, or both will allow a user to change the spectral output. Thus, a user can change the spectral output of a fluorescent concentrator system by changing the fluorescent concentrator body.

In one embodiment a user can select a pulse width and fluence through a user interface. Simpler versions of the device may not allow a pulse width selection. In more complex systems an interface along the lines described in US pending Publication No. 2005/0137655 filed Feb. 27, 2004, entitled SYSTEM AND METHOD FOR FLEXIBLE ARCHITECTURE FOR DERMATOLOGIC TREATMENTS UTILIZING MULTIPLE LIGHT SOURCES, can be provided which allows a user to select fluence levels and pulse width in accordance with the desired output therapeutic energy, which is to be transmitted from the output surface of the fluorescent concentrator body and to a target tissue area. A processor receives the user input, and drives a controllable power supply in accordance with the user input parameters, so that the illumination source, such as a flashlamp, LED array, or alternative light source, provides an appropriate pump energy to the fluorescent concentrator body. The pulse width should be in a range corresponding to the thermal relaxation times of epidermally-located structures to be treated. This typically places the pulse widths above 100 microseconds and less than 100 milliseconds. Fluence ranges for epidermal melanin will depend on the fluorescent concentrator spectral output, melanin concentration, type and localization. Approximate ranges are from 1-15 $J/cm^2$. For vascular treatments, generally the spectral range is determined by the hemoglobin absorption peaks that fall between 500 and 600 nm. Appropriate fluence may fall in the range between 5 and 50 $J/cm^2$.

Prior to initiating the firing of the controllable power supply the output surface of the fluorescent concentrator body is placed in contact with the selected area of tissue to be treated.

Of course, as discussed above, other designs could provide for using an optical delivery module, between the output of the fluorescent concentrator body and the area to be treated, and in some cases, near contact as opposed to direct contract with the targeted area may be used. After the light source is in position to deliver therapeutic energy to the selected area the controllable power supply is activated. Some systems could provide a user activated switch to control the firing of the power supply, other systems could also include generating light pulses on according to a timed interval. After application of the therapeutic energy the user may observe the treated area for the proper clinical endpoint. The endpoint may include immediate erythema, delayed erythema, immediate pigment color change, or immediate darkening or other color change of vascular structures. Once an area has been treated, the fluorescent concentrator can be repositioned for treating another area.

In addition to the above-described method, the operation of providing for some cooling to the area being treated could also be included. Indeed, epidermal cooling may be important for some applications, especially for higher fluences, larger spots, darker pigments or larger vascular structures. Epidermal cooling may be accomplished in several ways. One method of cooling provides for cooling the contacting element, which may either be the fluorescent concentrator itself, or an optical delivery module such as an optic fiber. Cooling the optical delivery system or the fluorescent concentrator itself may be accomplished by surrounding at least part of the delivery system or fluorescent concentrator body with an optical material or fluid held at a lower temperature. The epidermal cooling is then accomplished through conduction through either the fluorescent concentrator body, or the delivery system, which is in contact with target area which is being treated.

Appropriate choices of indices of refraction must be made for the cooling fluid or optical material conducting heat from the fluorescent concentrator body, or optical delivery module, and the fluorescent concentrator or delivery module materials in such a way as to produce the desired capture efficiency. The total internal reflection could be adversely impacted if the index of refraction for the fluorescent concentrator body is not a sufficiently higher index than the medium which surrounds it. Where direct contact epidermal cooling arrangement is used, cooling occurs as the fluorescent concentrator is positioned against the target area, and during the application of the therapeutic energy.

Figure 9:
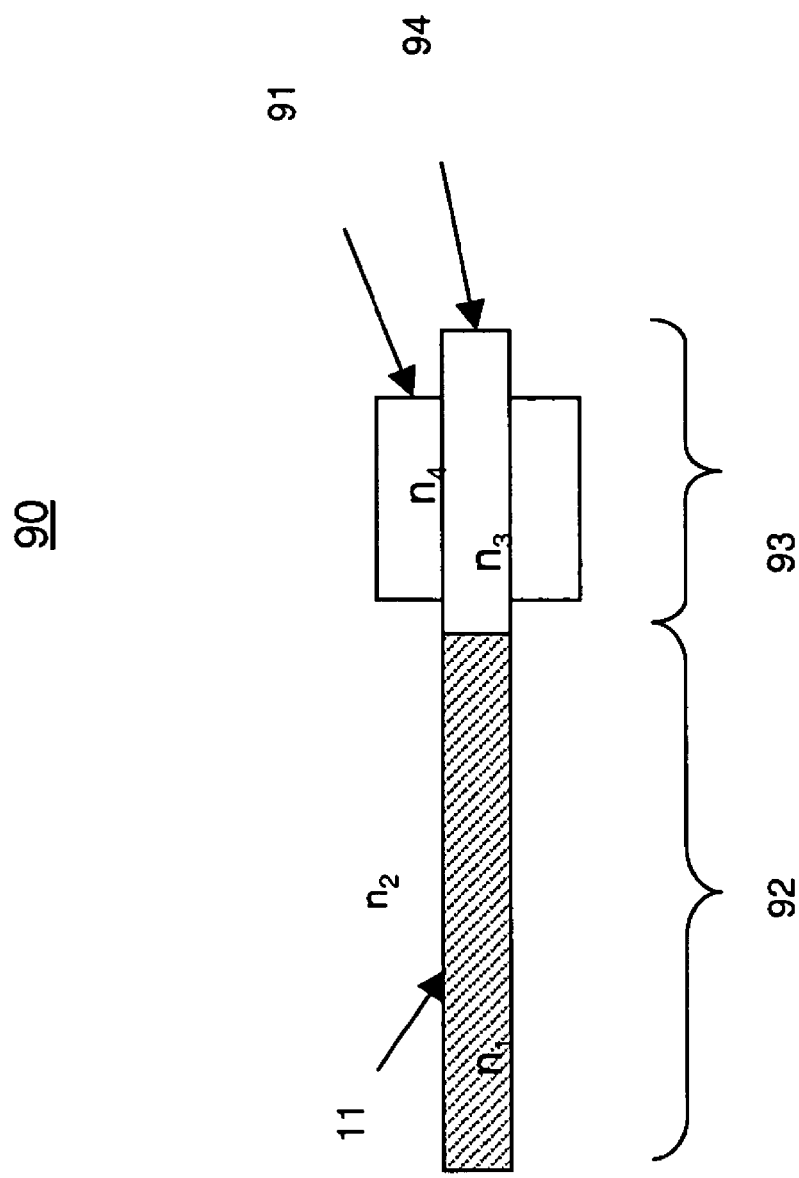
FIG. 9 shows an embodiment herein where a delivery tip is used to provide cooling to an area being treated.

Another possible approach for cooling is shown in the embodiment 90 of FIG. 9. In embodiment 90 a fluorescent concentrator body 11 is provided. A delivery tip 94 is provided which is coupled to the output surface of the fluorescent concentrator 11. In one embodiment the delivery tip 94 would be in contact with targeted area for treatment. One aspect of using a delivery tip 94, is that material of the delivery tip 94, can be selected such that its index of refraction $n_3$ relative to the index of refraction $n_4$ for the cooling material/fluid can provide for a desired capture efficiency as light moves from fluorescent concentrator body 11 to delivery tip 94 and through the delivery tip. That is, one desires capture efficiencies shown below for f->* and f-> to be similar. The material for the delivery tip can be selected with a desired index of refraction such that the index of refraction of the delivery tip $n_3$, and the index of refraction for the cooling medium $n_4$ yield a capture efficiency comparable of the for the fluorescent concentrator body 11 where it has an index of refraction of $n_1$ and is surrounded by a medium having an index of refraction of $n_2$. In one embodiment the material of the delivery tip 94** may thus be selected to provide a value for $n_3$ that may then be substantially larger than $n_1$ to achieve comparable capture efficiency values.

One example of an embodiment for device 90 as shown in FIG. 9 would provide for the material of the fluorescent concentrator body being PMMA having and index of refraction $n_1$, and the medium around fluorescent concentrator body 11 is air having an index of refraction of $n_2$. The material of the delivery tip is YAG or Saphire having an index of refraction of $n_3$, and the coolant 91 is water $n_4$, and the capture efficiencies for the area 92 is shown by the general equation below where f->*=0.16 and for the area 93 the capture fraction f->**=0.14, as given by the capture efficiency equations below:

$$f\text{->}* = [1-n2/n1]/2 = 0.16$$

$$f\text{->}** = [1-n4/n3]/2 = 0.14$$

Since the capture efficiencies are closely matched, the light captured in the fluorescent concentrator body 11, portion continues to be guided with good efficiency through the delivery tip 94 section of the device (where the delivery tip operates to provide the functions of transmitting light from the fluorescent concentrator body to the skin, and for providing skin contact cooling while the light is being delivered).

Figure 10B:
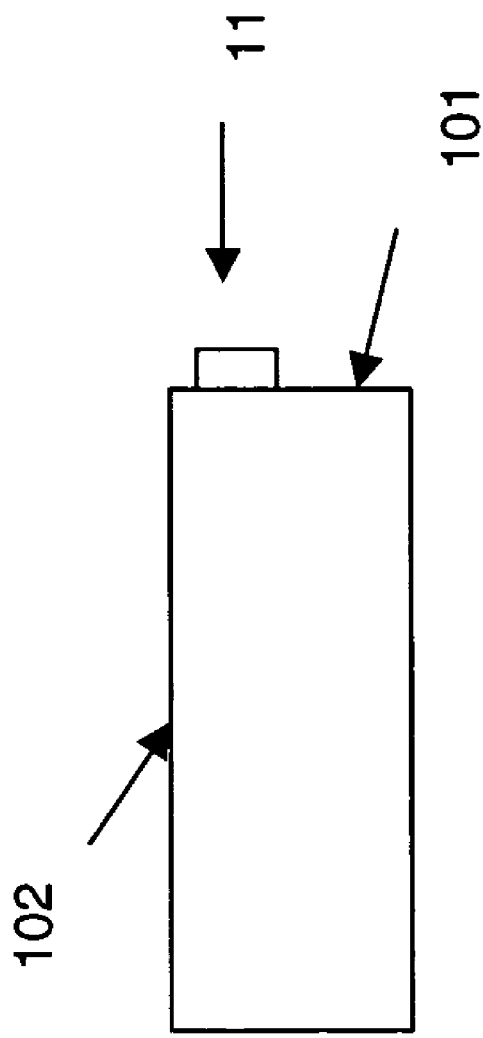
FIGS. 10a-b show views of an embodiment herein where a pre and/or post cooling fluorescent concentrator system is provided.
Figure 10A:
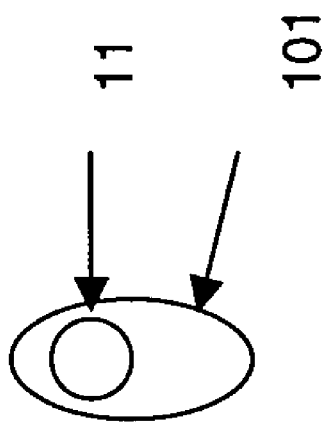

FIGS. 10A-10B show an alternative design for providing cooling to a target area being treated. The alternative system and method involves using a thermally conducting surface to pre- and/or post-cool the epidermis. FIG. 10B shows a side view of a housing 102 which contains at least a fluorescent concentrator body 11 which is optically pumped and outputs fluorescent light as therapeutic energy from a portion of the fluorescence concentrator 11 which protrudes from the housing 102. The cooling surface 101 can arranged immediately adjacent to the fluorescent concentrator output surface or delivery system, and could generally be in the same plane as the part of fluorescent concentrator which is in contact with the skin. Epidermal cooling is accomplished by contacting the targeted skin area first with the thermally conducting surface 101 for a proscribed amount of time, and then immediately repositioning the housing, which can shaped in the form of a hand piece, such that the delivery system or fluorescent concentrator output surface is ready to deliver light energy to the pre-cooled skin area. Alternatively, the skin area may be cooled immediately post-exposure by first positioning the delivery system or fluorescent concentrator contact tip, producing a light energy exposure, and then repositioning the applicator or hand piece to allow contact cooling with the thermally conducting surface. General aspects of a system and method for pre and post cooling in connection with light treatments to the skin area described in U.S. Pat. Nos. 6,383, 176 and 6,485,484 which are incorporated herein by reference.

Figure 5:
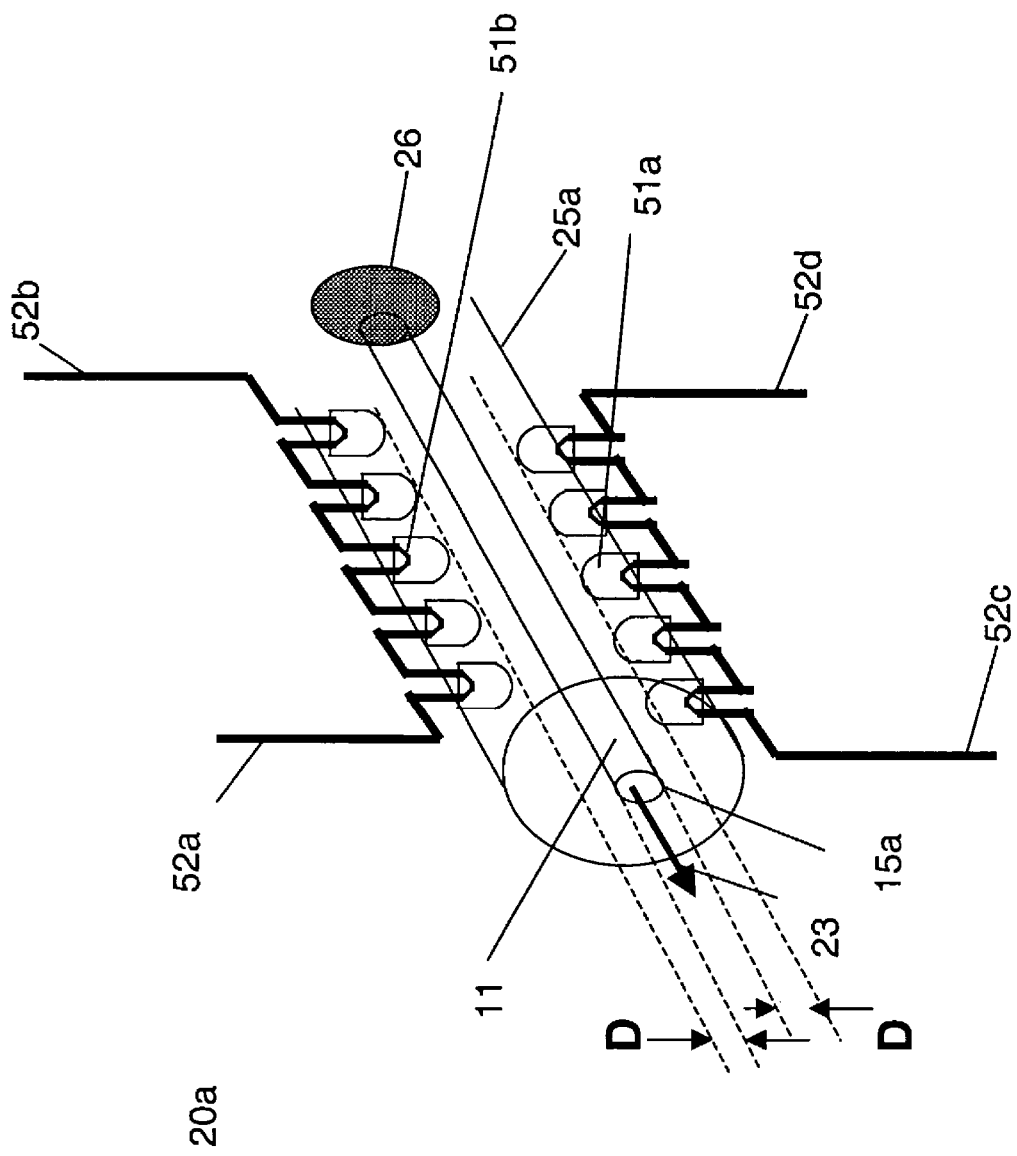
FIG. 5 shows a perspective view of a fluorescence concentrator system of an embodiment herein using two linear arrays of dome style LED packages as the illumination source.

The fluorescence concentrator system herein can utilize any of broad range of different light sources. One alternative embodiment of a fluorescence concentrator system 20a using dome style LED packages as an illumination source is shown in FIG. 5. This embodiment is similar to flashlamp-pumped fluorescence concentrator 20 shown in FIG. 2 except that the single flashlamp illumination source has been replaced by two linear arrays of dome style LEDs 51a and 51b. A reflector structure 25a has a series of apertures through which the individual LEDs in arrays 51a and 51b protrude. The distance D between the top of the domes on LED arrays 51a and 51b and fluorescence concentrator 11 is comparable to or less than the diameter of fluorescence concentrator 11. LED arrays 51a and 51b are positioned on opposing sides of fluorescence concentrator 11. LED arrays 51a and 51b are laterally offset from each other, so that reflector structure 25a intercepts the majority of pump light which initially misses fluorescence concentrator 11. Reflective structure 25a need not have a simple featureless surface as shown in FIG. 5, but may consist of a plurality of individual reflectors opposite each LED in arrays 51a and 51b. A reflective surface 26 is provided on the fluorescence concentrator face opposing end surface 15a. Reflector structure 25a and reflective surface 26 increase fluorescence concentrator system 20a efficiency. Output light 23 is emitted by end surface 15a. Tens or even hundreds of individual dome style LEDs can be used in linear arrays 51a and 51b. The multiple LEDs compromising linear LED arrays 51a and 51b are connected electrically in series, although a combination of parallel and series electrical connections can be used. The required electrical power to drive LED arrays 51a and 51b is supplied through LED electrical leads 52a, 52b, 52c and 52d. Additionally, although the light sources are shown as linear arrays, other non-linear configurations of LEDs could be used.

Given the performance of most present LEDs, multiple LEDs are generally required as an illumination source in the fluorescence concentrator system 20a since the maximum power attainable from a single LED is relatively small. One relatively high power LED currently available is the Royal Blue Luxeon V LED available from Lumileds Lighting of San Jose, Calif. These LEDs have a rated continuous power output of 500 mW and an emission wavelength in the vicinity of 450 nm. The output spectral width is typically 20 nm to 30 nm. These LEDs have a 2 mm×2 mm semiconductor die encapsulated in a roughly hemispherical dome with a radius of 2.8 mm. To attain the rated power they require a drive voltage of approximately 6.8 Volts and a drive current of 700 mA.

LEDs are intrinsically continuous wave (cw) sources, however, their output can easily be pulsed by energizing them with a pulsed drive current. When using arrays 51a and 51b at low duty cycles, such as 1%, it is possible to run them at currents and output powers significantly above their rated cw levels. For Royal Blue Luxeon V LEDs, Lumileds part #LXHL-LR5C, output powers approximately three times the rated cw power for 20 msec long pulses have been demonstrated. For shorter pulse lengths higher operating power can be obtained.

In one embodiment an LED pumped concentrator system 20a was implemented using two rows of Royal Blue Luxeon V Star LEDs with eleven LEDs in each row. Each LED array 51a and 51b was approximately 11 cm long. The individual LEDs in the arrays were separated by slightly less than 1 cm. The LEDs were used to pump a 126 mm long, 1 mm diameter fluorescence concentrator fabricated from Bicron part number # 693-00001 fluorescent fiber. Operating arrays 51a and 51b at three times their rated cw currents generated 33 W of pump light in a 20 msec pulse, yielded a pump energy of 0.66 Joules. Fluorescence concentrator output light 23 was 1.4 W, resulting in an intensity of 178 W/cm$^2$ and an optical fluence of 3.5 J/cm$^2$. This level of intensity and fluence is relatively low for a number of photothermolysis based therapeutic treatments but the intensity can be increased by using more or higher power LEDs in arrays 51a and 51b. The fluence can also be increased by increasing the pulse width, although pulses longer than 50 msec are generally not useful in photothermolysis based treatments for structures targeted in dermatological treatments. However, these intensity and fluence levels may be useful in treatment protocols that utilize a photochemical response, for example, photodynamic therapy. Further, other embodiments could use additional arrays LEDs disposed around the fluorescence concentrator to further increase the output optical fluence.

Figure 6:
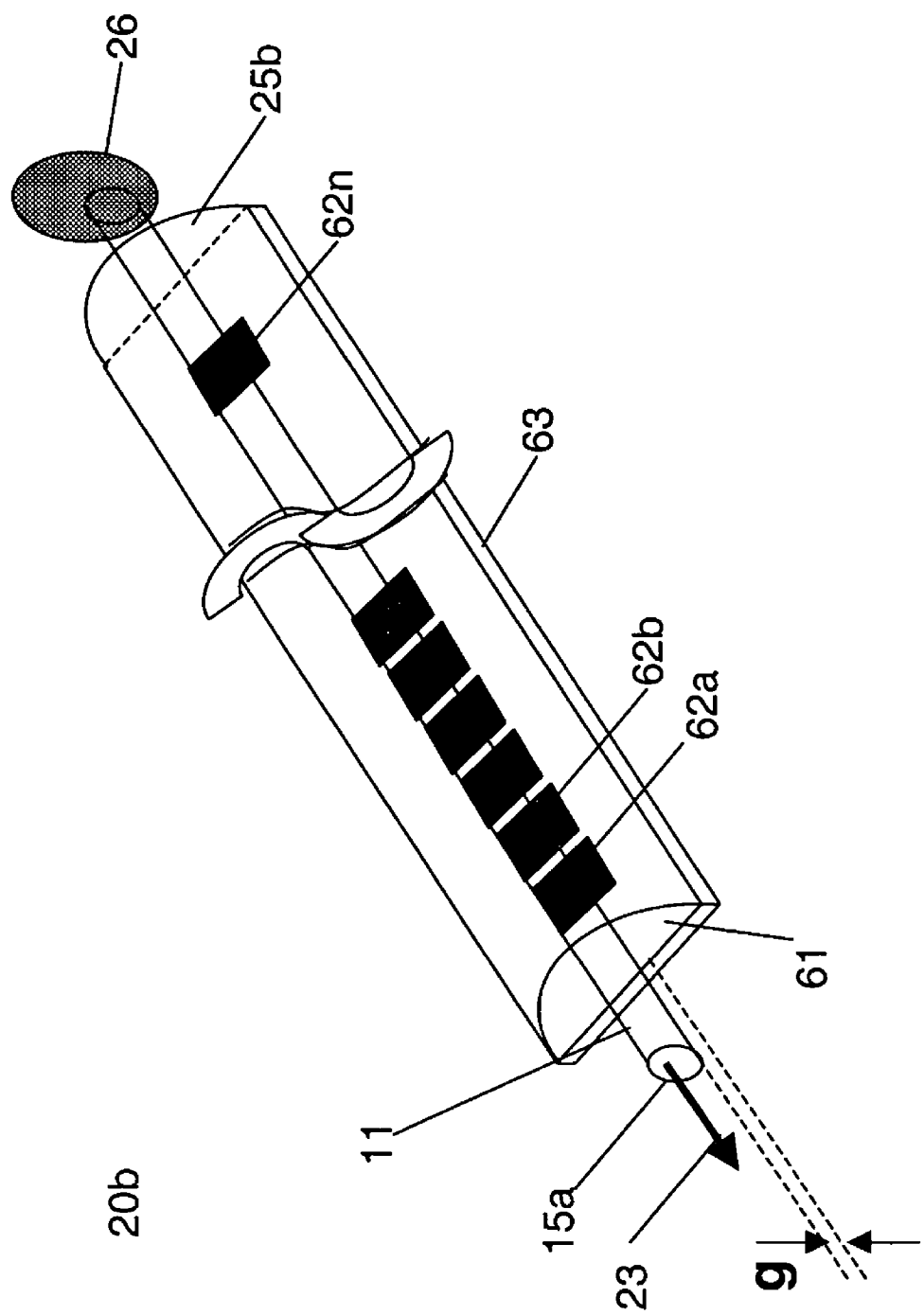
FIG. 6 shows a perspective view of a fluorescence concentrator system of an embodiment herein using a linear array of flat style LED packages as the illumination source.

A further alternative embodiment of a fluorescence concentrator system 20b using flat package style LEDs is shown in FIG. 6. A linear array of flat packaged LEDs 61 is used as the illumination source. Linear array 61 consists of a plurality of individual LED die 62a, 62b ... 62n mounted on a common base 63. The die are encapsulated with a thin sealant, producing an array emitting surface that is approximately flat. Linear array 61 may consist of tens or even hundreds of die which are closely spaced along the axis of fluorescence concentrator 11. Prototypes of these arrays are available from PRP Optoelectronics located in Towcester, England. The distance (g) between the emitting surface of array 61 and fluorescence concentrator 11 is comparable to or less than diameter of fluorescence concentrator 11. A reflective structure 25b is located above LED array 61 and surrounds fluorescence concentrator 11. A reflective surface 26 is provided on the fluorescence concentrator face opposing end surface 15a. Output light 23 is emitted by end surface 15a.

Flat package style LED array 61 is an advantageous pump source for system 20b since the distance between LED die 62a, 62b ... 62n and fluorescence concentrator 11 can be quite small, typically less than 2 mm. This improves the coupling efficiency of pump light emitted by die 62a, 62b, ... 62n into fluorescence concentrator 11. The die 62a, 62b ... 62n have a high packing density long the axis of concentrator 11. This allows for high pump powers per unit length of concentrator 11, improving the efficiency of system 20b.

Figure 7:
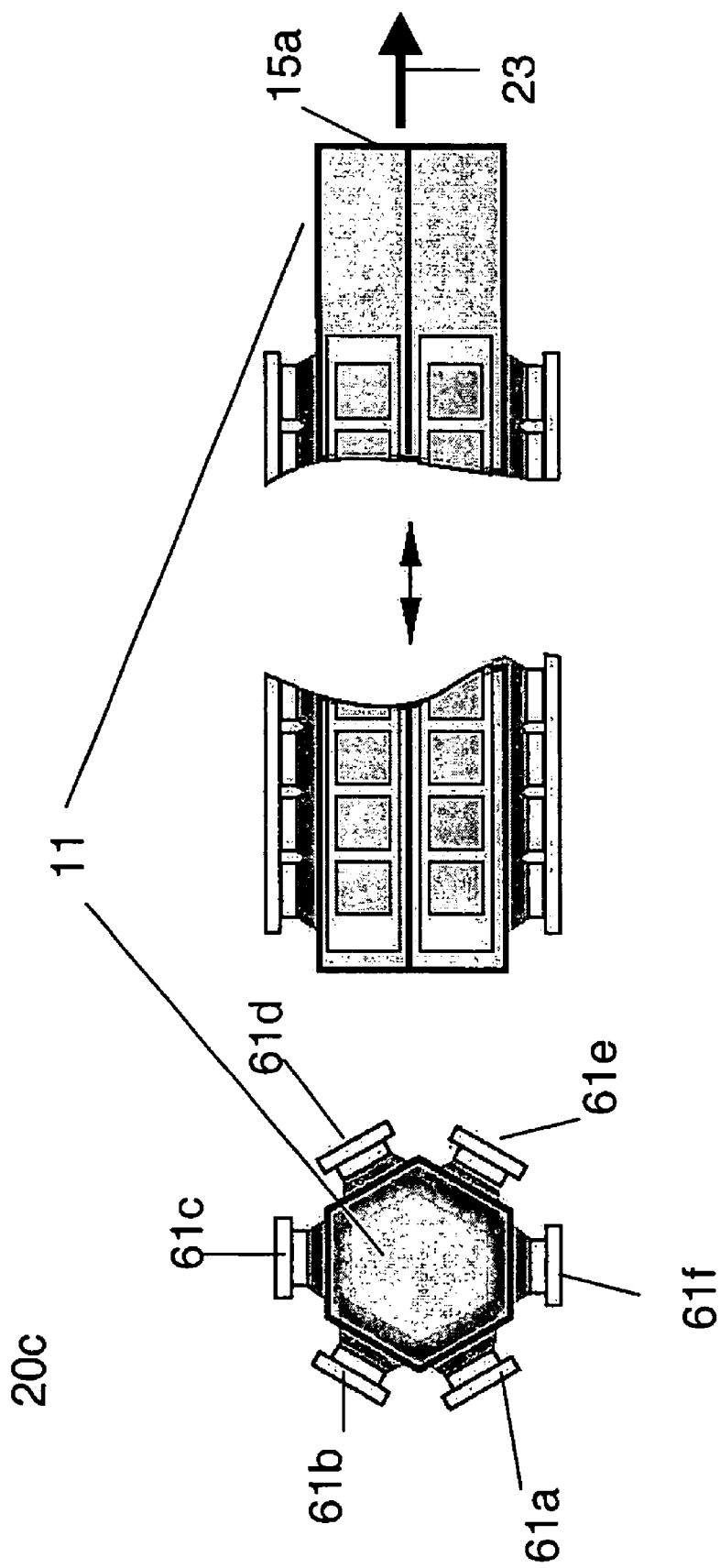
FIG. 7a shows an end view of fluorescence concentrator system of an embodiment herein using multiple linear arrays of flat style LED packages as the illumination source.
FIG. 7b shows a side view of fluorescence concentrator system of an embodiment herein using multiple linear arrays of flat style LED packages as the illumination source.

A further alternative embodiment of a fluorescence concentrator system 20c using a plurality of flat style package linear LED arrays is shown in FIGS. 7a (end view) and 7b (side view). Six linear arrays 61a, 61b, 61c, 61d, 61e, and 61f are closely positioned in a hexagonal pattern around hexagonally-shaped fluorescence concentrator 11. The distance between emitting surface of arrays 61a thru 61f and fluorescence concentrator 11 may be larger in this embodiment than in other embodiments to facilitate placement of multiple arrays, but this distance is shown in FIG. 7a and 7b as being quite short. A reflective structure surrounding fluorescence concentrator 11 and a reflective surface opposite the concentrator end surface 15a could be used with this embodiment, but are not shown in FIG. 7. Output light 23 is emitted from end surface 15a.

An advantage of system 20c is that it allows pumping from all sides of fluorescence concentrator 11. This allows a high pump density per unit length along concentrator 11, facilitating high output intensities or use of short concentrators. Since each system 20c requires six arrays 61a thru 61f, economies of scale could be achieved in manufacturing the arrays, reducing the system cost.

Figure 8:
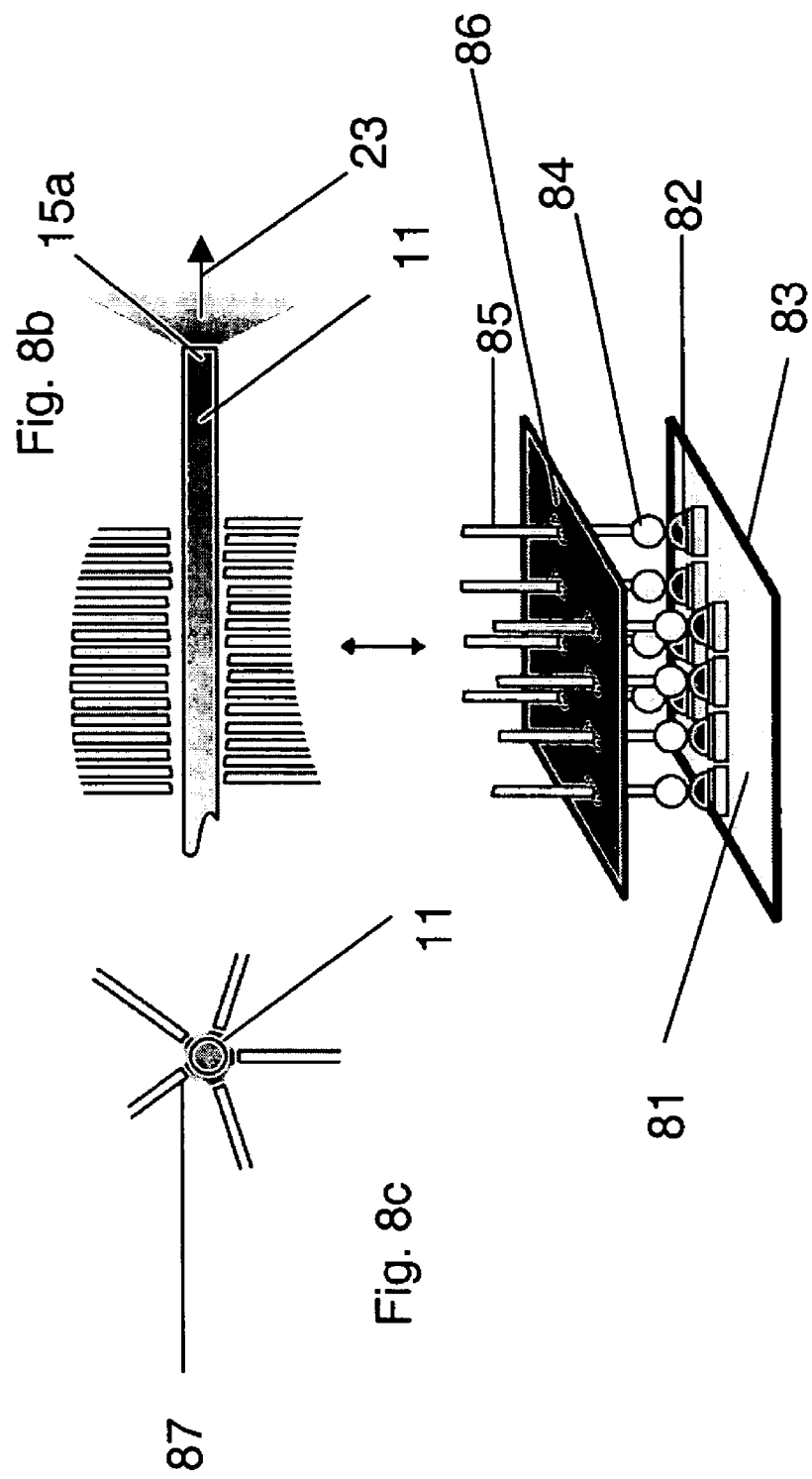
FIGS. 8a-c show different views of an embodiment herein of a fluorescence concentrator system using multiple, fiber-delivered LEDs as the illumination source.

A further alternative embodiment of a fluorescence concentrator system 20d using a two-dimensional LED array 81 as the illumination source is shown in FIGS. 8A-C. Additional details regarding two-dimensional LED arrays are discussed in pending U.S. patent application Ser. No. 10/171, 101 (Publication No. 2003/0233138) filed Jun. 12, 2002, and which is incorporated herein by reference. Array 81 has individual LEDs 82 placed in a regular grid on mounting plate 83. Individual LEDs 82 could utilize a dome style package, flat style package, or could use an alternative package style. Positioned proximal to the output surface of LEDs 82, lenses 84 capture light emitted from LEDs 82 and direct it into optical fibers 85. Spacing grid 86 holds fibers 85 and aligns them on a regular grid, so that all fibers 85 are simultaneously aligned to LEDs 82 on array 81. The ends 87 of fibers 85 are positioned adjacent to fluorescence concentrator 11 such that the spacing between them is less than or comparable to the diameter of concentrator 11. FIG. 8b shows that along the axis of concentrator 11 fibers 85 are positioned touching or immediately adjacent to each other. A reflective structure surrounding fluorescence concentrator 11 and a reflecting surface opposite the concentrator end surface 15a could be used with this embodiment, but are not shown in FIG. 8b. Output light 23 is emitted from end surface 15a. FIG. 8c shows that the ends 87 can be position about an axis of the fluorescent concentrator.

The emission of LED array 81 is delivered to fluorescence concentrator 11 via fibers 85. This advantageously allows fluorescence concentrator system 20d to have an LED array 81 efficiently pump concentrator 11 while the two are spatially separated. Unlike other embodiments, the regular LED grid on array 81 can have an arbitrary layout, independent of the shape of concentrator 11. The light emitted from the ends of fibers 85 can very efficiently couple into fluorescent concentrator 11, since fibers 85 can be positioned on different sides of concentrator 11 and are closely packed together. Even though the coupling efficiency from LED array 81 into fibers 85 may be low, the overall system efficiency could be comparable to other fluorescence concentrator system embodiments because the coupling between fluorescent concentrator 11 and the ends of fibers 85 can be made quite high.

Other optical methods could be used to deliver light from the LED array 81 to the fluorescent concentrator 11. The delivery means could be by an array of waveguides or lens. These optical systems could be configured to transform the emission pattern from array 81 into an emission pattern that efficiently couples into concentrator 11.

Many other variants to the basic fluorescence concentrator system can be utilized. A multi-staged concentrator could be used to further increase brightness. This system would use the output of one fluorescence concentrator system to pump another fluorescence concentrator. The fluorescence concentrator cross-section could be a tube and the illumination source could be located within the tube. This variant would have a high coupling efficiency between the illumination source and fluorescence concentrator and may not benefit from a reflective structure. A further system variant would include the use of a fluorophore dissolved in a liquid contained within a transparent tube. In this case the tube outer walls act as a guiding interface in addition to the tube inner wall/liquid interface. A further system variant is use of two fluorophores in a fluorescence concentrator. The fluorescence of one fluorophore overlaps the pump bands of the other fluorophore, effectively increasing the spectral width of the concentrator pump bands. Such a variant is particularly advantageous when used with a flashlamp illumination source, which has a broad emission spectra. A further variant is the use of multiple fluorescence concentrators in a single fluorescence concentrator system. The outputs from the multiple concentrators could be advantageously bundled to produce a collective end cross-section that optimizes treatment. Such a cross-section might be a line or a circle. A further system variant uses a fluorescence concentrator with a varying cross-sectional profile along its length. The profile could be simultaneously optimized for pump collection efficiency and distal surface cross-section. The transitions between the profiles must be gradual and the overall cross-sectional area must be approximately constant throughout the length of the concentrator to avoid excessive optical loss.

As is apparent from the preceding description a high brightness fluorescence concentrator system has many advantages. Relative to some laser systems it is capable of generating high powers at visible wavelengths. For example, output powers exceeding 30 KW in the green spectral region have been achieved. Unlike laser systems many potential fluorophores can be used providing near continuous wavelength coverage across the visible spectrum with a single system architecture. This can be achieved by using different fluorophores which output different wavelengths of optical energy.

Relative to flashlamps or filtered flashlamps, fluorescence concentrator systems offer significantly higher spectral brightness and a much better localized output spot. Relative to LEDs, fluorescence concentrator systems offer significantly higher brightness, allowing generation of intensities suitable for photothermolysis-based treatments.

In addition to the medical field, high brightness fluorescence concentrators systems could be used in any application requiring optical intensities exceeding 10 $W/cm^2$. Examples of such applications include use as a high intensity indicator light, a warning light, or a pump source for an optically-pumped laser.

One of the many advantageous and unique characteristic of the system and method herein is that an optical energy source is provide where the source of the optical energy can be in direct contact with the skin or other tissue to be treated. This is in contrast with other therapeutic light sources in which the device or material generating light is separated by a series of optical or mechanical elements. Thus, the fluorescent concentrator can operate to provide a simpler and less expensive treatment device, by virtue of being able to eliminate components that are required in other systems.

Another potential advantage of embodiments herein is that they can provide for enhanced eye safety. Generally, embodiments of the fluorescent concentrator system herein will provide for high divergence, small spot size and lack of coherence of light, and this combination of characteristics makes such a system eye safe even at distances of a few millimeters. This means that areas of tissue in close proximity to the eyes can be treated, whereas lasers, and flashlamps are not used close to a patient's eyes due to the high risk of the eye injury.

While various embodiments of the present invention have been described above, it should be understood that they have been presented by way of example, and not limitation. It will be apparent to persons skilled in the relevant art that various changes in form and detail may be made therein without departing from the spirit and scope of the invention. This is especially true in light of technology and terms within the relevant art(s) that may be later developed. Thus, the present invention should not be limited by any of the above-described exemplary embodiments, but should be defined only in accordance with the following claims and their equivalents. Further, while the invention has been described primarily with reference to medical aesthetic procedures, it could also be useful for other applications which require a high intensity optical source.

Any and all patents, patent applications and printed publications referred to above are incorporated by reference.

We claim:

1. A fluorescence concentrator system comprising:
an illumination source for generating pump light;
a body which includes a fluorophore, said body being positioned to receive the pump energy from the illumination source, and wherein the fluorophore outputs fluorescent energy in response to the pump energy and wherein the body is shaped to concentrate at least a fraction of the fluorescent energy to an output surface of the body, the fraction of the fluorescent energy at the output surface being transmitted from the output surface as a therapeutic energy and wherein the spectral intensity of the fluorescent energy at the output surface of the body is greater than the spectral intensity of the pump light; and an optical delivery module which receives the therapeutic energy from the output surface and transmits it to an area of tissue to be treated, wherein the therapeutic energy has an intensity of at least 10 W/cm2.

2. The system of claim 1, further including a reflective structure surrounding at least a portion of the illumination source and a portion of the body.

3. The system of claim 1, wherein the illumination source includes a flashlamp.

4. The system according to claim 1, wherein the illumination source includes a plurality of light emitting diodes.

5. The system of claim 1, wherein the output surface has a first area, and wherein the body includes a second area which receives the pump light, and wherein the second area is greater than the first area.

6. The system of claim 5, wherein the first area is less than one-tenth of the second area.

7. The system of claim 1, wherein the body has a substantially cylindrical shape and the output surface is defined by a first end of the cylindrical shape.

8. The system of claim 1, wherein the body includes a core which has a first index of refraction and the body includes a cladding which surrounds the core, and the cladding has a second index of refraction, and wherein the first index of refraction is greater than the second index of refraction.

9. The system claim 1, wherein the therapeutic energy has a spectral intensity at least 50 times greater than the spectral intensity of the pump energy.

10. A fluorescence concentrator system comprising:

an illumination source for generating pump light; and a body which includes a fluorophore, said body being positioned to receive the pump energy from the illumination source, and wherein the fluorophore outputs fluorescent energy in response to the pump energy and wherein the body is shaped to concentrate at least a fraction of the fluorescent energy to an output surface of the body, the fraction of the fluorescent energy at the output surface being transmitted from the output surface as a therapeutic energy and wherein the spectral intensity of the fluorescent energy at the output surface of the body is greater than the spectral intensity of the pump light and wherein the therapeutic energy has an intensity of at least 10 W/cm$^2$.

11. The system of claim 10, further including an optical delivery module which receives the therapeutic energy from the output surface and transmits it to an area of tissue to be treated.

12. The system of claim 10, further including a reflective structure surrounding at least a portion of the illumination source and a portion of the body.

13. The system of claim 10, wherein the illumination source includes a flashlamp.

14. The system according to claim 10, wherein the illumination source includes a plurality of light emitting diodes.

15. The system claim 10, wherein the therapeutic energy has a spectral intensity at least 50 times greater than the spectral intensity of the pump energy.

* * * * *